US 6,743,290 B2

(12) United States Patent
Dahl et al.

(10) Patent No.: US 6,743,290 B2
(45) Date of Patent: *Jun. 1, 2004

(54) COMPOSITIONS COMPRISING UNDECAMANTANES AND PROCESSES FOR THEIR SEPARATION

(75) Inventors: Jeremy E. Dahl, Palo Alto, CA (US); Robert M. Carlson, Petaluma, CA (US)

(73) Assignee: Chevron U.S.A. Inc., San Ramon, CA (US)

( * ) Notice: Subject to any disclaimer, the term of this patent is extended or adjusted under 35 U.S.C. 154(b) by 174 days.

This patent is subject to a terminal disclaimer.

(21) Appl. No.: 10/012,336

(22) Filed: Dec. 12, 2001

(65) Prior Publication Data

US 2002/0139295 A1 Oct. 3, 2002

Related U.S. Application Data

(60) Provisional application No. 60/262,842, filed on Jan. 19, 2001.

(51) Int. Cl.[7] .................................................. C30B 7/08
(52) U.S. Cl. ........................ 117/68; 117/64; 117/70; 117/925; 117/926; 117/927; 117/929; 585/21
(58) Field of Search ............................ 117/68, 69, 70, 117/925, 926, 927, 929; 585/21

(56) References Cited

U.S. PATENT DOCUMENTS

| | | |
|---|---|---|
| 3,457,318 A | 7/1969 | Capaldi |
| 3,832,332 A | 8/1974 | Thompson |
| 4,952,748 A | 8/1990 | Alexander |
| 4,952,749 A | 8/1990 | Alexander |
| 4,952,757 A | 8/1990 | Alexander |
| 4,982,049 A | 1/1991 | Alexander |
| 5,017,734 A | 5/1991 | Baum |
| 5,019,665 A | 5/1991 | Partridge |
| 5,245,104 A | 9/1993 | Cullick |
| 5,268,513 A | 12/1993 | Shen |
| 5,298,666 A | 3/1994 | Shen |
| 5,306,851 A | 4/1994 | Wu |
| 5,347,063 A | 9/1994 | Shen |
| 5,369,213 A | 11/1994 | Shen |
| 5,380,947 A | 1/1995 | Chen |
| 5,382,684 A | 1/1995 | Moini |
| 5,397,488 A | 3/1995 | Chen |
| 5,410,092 A | 4/1995 | Shen |
| 5,414,189 A | 5/1995 | Chen |
| 5,430,193 A | 7/1995 | Shen |
| 5,461,184 A | 10/1995 | Swanson |
| 5,498,812 A | 3/1996 | Bradway |
| 5,576,355 A | 11/1996 | Chen |
| 6,235,851 B1 | 5/2001 | Ishii |

FOREIGN PATENT DOCUMENTS

| | | |
|---|---|---|
| EP | 0399851 | 11/1996 |
| WO | WO 95/11472 | 4/1995 |

OTHER PUBLICATIONS

Aczel, et al., "Stability of Adamantane and its Derivatives to Coal–liquefaction Conditions, and its implications toward the organic structure of Coal", *Fuel*, vol. 58, pp. 228–230, (Mar. 1979).

Balaban, et al., Systemic Classification and Nomenclature of Diamond Hydrocarbons–I, *Tetrahedron*, 34, pp. 3599–3606, (1978).

(List continued on next page.)

*Primary Examiner*—Robert Kunemund
(74) *Attorney, Agent, or Firm*—Burns Doane Swecker & Mathis, LLP

(57) ABSTRACT

Disclosed are compositions comprising one or more undecamantanes. Specifically disclosed are compositions comprising 25 to 100 weight percent of one or more undecamantanes. Also disclosed are novel processes for the separation and isolation of undecamantane components into recoverable fractions from a feedstock containing at least a higher diamondoid component which contains one or more undecamantane components.

42 Claims, 30 Drawing Sheets

OTHER PUBLICATIONS

Badziag, P., et al., "Nanometre–sized Diamonds are More Stable than Graphite", *Nature*, vol. 343, pp. 244–245, and 517.

Bagrii, Ye, et al., "Catalytic Breakdown of Paraffinic Hydrocarbons in the Presence of Adamantanes", *Petrol. Chem USSR*, vol. 30, No. 2, pp. 131–134, (1990).

Chung, et al., Recent Development in High–Energy Density Liquid Fuels, *Energy and Fuels*, 13, pp. 641–649, (1999).

Dahl, J., et al., Diamondoid Hydrocarbons as Indicators of Natural Oil Cracking, *Nature*, 399, pp. 54–57, (1999).

Drexler, Eric K., *Nanosystems: Molecular Machinery Manufacturing and Computation*, John Wiley & Sons, pp. 238–249, (1992).

Fort, Jr., et al., Adamantane: Consequences of the Diamondoid Structure, *Chem. Rev.*, 64, pp. 277–300, (1964).

Hala, V.S., et al., "Analyse Unds erwendung on Pyrolyseol", *Jahrgang*, pp. 85–87, (Feb. 1971) In German–English Abstract on page 85.

Landa, S., "Adamantane and Its Homologues", *Current Science*, Gangalore, India, Vo. 32, pp. 485–489 (1963).

Lin, et al., Natrual Occurrence of Tetramantane ($C_{22}H_{36}$), Pentamantane ($C_{26}H_{32}$), and Hexamantane ($C_{30}H_{36}$) in a Deep Petroleum Reservoir, *Fuel*, 74:10, pp. 1512–1521, (1995).

McKervey, Synthetic Approaches to Large Diamondoid Hydrocarbonds, *Tetrahedron*, 36, pp. 971–992, (1980).

Machacek, V., et al., "Let Od Objeveni Adamantanu", *Chemicke Listy/svazek*, pp. 753–761, (1982) Russian—English Abstract on p. 761.

Oya, A, et al., "Carbonization of Adamantanes to a Graphitizable Carbon", *Fuel*, vol. 60, pp. 667–669, (Aug. 1981).

Petrov, A., "Hydrocarbons of Adamantane Series as Indicies of Petroleum Catagenesis Process", *Advances in Organic Geo Chemistry*, 6th International Meeting on Organic Geochemistry, pp. 517–522 (1973).

Prusova, D., Liquid Chromatography of Adamantanes and Carbon Adsorbents, *J. Chrom*, 234, pp. 1–11, (1982).

Rollman, L., et al., "Adamantanes From Petroleum, with Zeolites", American Chemical Study, 210th ACS National Meeting, Abstract and paper, Aug. 20, 1995).

Sandia National Laboratories (2000), World's First Diamond Micromachines Created at Sandia, Press Release, (Feb. 22, 2000), www.Sandia.gov.

Schleyer, P., et al., "Nonacyclo[$11.7.1.1^{2,18}.0^{3,16}.0^{4,13}.0^{5,10}.0^{6,14}.0^{7,11}.0^{15,20}$]–Docosane, a Bastard Tetramantane", *J. of the Am. Chem. Soc.*, 90:8, letter to the editor, Aug. 28, 1968.

Shen, M., et al., Finite $T_d$ Symmetry Models for Diamond: From Adamantane to Superadamantane ($C_{35}H_{36}$), *J. Am., Chem. Soc.*, vol. 114, No. 2, pp 497–505, (1992).

Supryadkina, NY, et al., "Catalytic Dealkylation of Alkyladamantanes", *Petrol. Chem., USSR*, vol. 28, No. 2, pp. 103–110, (1988).

Tominaga, K., et al., "Next–generation Fine Chemicals Raw Material–Adamantane", *Chem Econ & Eng. Review*, vol. 17, No. 10, pp. 23–29, (Oct. 1985).

Vodicka, L, et al., "High Performance Liquid Chromatography of Halogeno Derivatives of Adamantane and Diamantane", *J. Chrom*, 270, pp. 199–205, (1983).

Wingert, W., "G.e.–m.s. Analysis of Diamondoid Hydrocarbons in Smackover Petroleums", *Fuel*, vol. 71, pp. 37–42, (Jan. 1992).

Example of Symmetrical
Undecamantanes,
[123(1,2)42143]
Undecamantane

Examples of
Enantiomeric
Undecamantanes

*

* Mirror plane indicating enantiomeric pair

A)

B)

A) Hexamantanes & Heptamantanes

Parr Reaction No. 5,
Product from
FSL 8691,
Fraction #7

Undecamantanes

B)

Starting Material
FSL 8691,
Fraction #7

GC Time (min.) →

A)

B)

A)

B)

A)

B)

A)

B)

Heptamantane #1 Crystals

Heptamantane #2
Crystals

A)

B)

A) Crystal of Fully Condensed Decamantane

B) Mass Spectrum of Dissolved Crystal of Fully Comndensed Decamantane
Retention time 18.54 min.

[123(1,2)42143] Undecamantane A

Formula: $C_{39}H_{40}$
Symmetry:
Molecular Weight 508.749
Molecular Weight (Exact) 508.3130015

Carbon Framework

CPK Representation

[123(1,2)42143] Undecamantane A

View into Specified Diamond Crystal Lattice Plane

| 111 | 110 | 100 |

Undecamantane B

Formula: $C_{39}H_{40}$
Symmetry: $C_s$
Molecular Weight 508.749
Molecular Weight (Exact) 508.3130015

Carbon Framework

CPK Representation

Name: Undecamantane
Symmetry: $C_1$
Formula: $C_{41}H_{42}$
Molecular Weight 534.787
Molecular Weight (Exact) 534.3286516

Carbon Framework

CPK Representation

Name: Undecamantane
Symmetry: $C_1$
Formula: $C_{42}H_{44}$
Molecular Weight 548.814
Molecular Weight (Exact) 548.3443016

Carbon Framework

CPK Representation

Name: Undecamantane

Formula: $C_{42}H_{44}$
Molecular Weight: 548.814
Molecular Weight (Exact): 548.3443016

Carbon Framework

CPK Representation

Name: Undecamantane
Symmetry: $C_1$
Formula: $C_{45}H_{48}$
Molecular Weight 588.878
Molecular Weight (Exact) 588.3756018

Carbon Framework

CPK Representation

Name: Undecamantane
Symmetry: $C_1$
Formula: $C_{46}H_{50}$
Molecular Weight 602.905
Molecular Weight (Exact) 602.3912518

Carbon Framework

CPK Representation

Name: Undecamantane
Symmetry: $C_1$
Formula: $C_{48}H_{52}$
Molecular Weight 628.943
Molecular Weight (Exact) 628.9069019

Carbon Framework

CPK Representation

Name: Undecamantane
Symmetry: $C_1$
Formula: $C_{49}H_{54}$
Molecular Weight: 642.970
Molecular Weight (Exact): 642.4225520

Carbon Framework

CPK Representation

Name: Undecamantane
Symmetry: C$_{2v}$
Formula: C$_{50}$H$_{56}$
Molecular Weight 656.997
Molecular Weight (Exact) 656.4382021

Carbon Framework

CPK Representation

COMPOSITIONS COMPRISING UNDECAMANTANES AND PROCESSES FOR THEIR SEPARATION

REFERENCE TO RELATED APPLICATIONS

This application claims priority under 35 USC 1.119(e) to U.S. Provisional Application Serial No. 60/262,842 filed Jan. 19, 2001 which is incorporated by reference.

BACKGROUND OF THE INVENTION

1. Field of the Invention

This invention is directed to novel compositions comprising undecamantanes. This invention is also directed to novel processes for the separation and isolation of undecamantane components into recoverable fractions from a feedstock containing at least one or more undecamantane components.

REFERENCES

The following publications and patents are cited in this application as superscript numbers:

1. Lin, et al., *Natural Occurrence of Tetramantane ($C_{22}H_{28}$), Pentamantane ($C_{26}H_{32}$) and Hexamantane ($C_{30}H_{36}$) in a Deep Petroleum Reservoir*, Fuel, 74(10):1512–1521 (1995).
2. Alexander, et al., Purification *of Hydrocarbonaceous Fractions*, U.S. Pat. No. 4,952,748, issued Aug. 28, 1990.
3. McKervey, *Synthetic Approaches to Large Diamondoid Hydrocarbons*, Tetrahedron, 36:971–992 (1980).
4. Wu, et al., *High Viscosity Index Lubricant Fluid*, U.S. Pat. No. 5,306,851, issued Apr. 26, 1994.
5. Chung et al., *Recent Development in High-Energy Density Liquid Fuels*, Energy and Fuels, 13, 641–649 (1999).
6. Sandia National Laboratories (2000), *World's First Diamond Micromachines Created at Sandia*, Press Release, (Feb. 22, 2000) www.Sandia.gov.
7. Balaban et al., *Systematic Classification and Nomenclature of Diamondoid Hydrocarbons-I*, Tetrahedron. 34, 3599–3606 (1978).
8. Chen, et al., Isolation *of High Purity Diamondoid Fractions and Components*, U.S. Pat. No. 5,414,189 issued May 9, 1995.

All of the above publications and patents are herein incorporated by reference in their entirety to the same extent as if each individual publication or patent was specifically and individually indicated to be incorporated by reference in its entirety.

2. State of the Art

Undecamantanes are bridged-ring cycloalkanes. They are the face-fused undecamers of adamantane (tricyclo[3.3.1.1$^{3,7}$]decane) or $C_{10}H_{16}$ The compounds have a "diamondoid" topology, which means their carbon atom arrangement is superimposable on a fragment of the diamond lattice (FIG. 1). Undecamantanes possess eleven of the "diamond crystal units" and therefore, it is postulated that there are hundreds of possible undecamantane structures which exist in different molecular weight core structures. Among them, there are undecamantanes having the molecular formula $C_{39}H_{40}$ (molecular weight 508) of which two are structurally compact in relation to the other undecamantanes. Undecamantanes also have the molecular formulas: $C_{50}H_{56}$ (molecular weight 656), $C_{49}H_{54}$ (molecular weight 642), $C_{48}H_{52}$ (molecular weight 628), $C_{46}H_{50}$ (molecular weight 602), $C_{46}H_{48}$ (molecular weight 588), $C_{42}H_{44}$ (molecular weight 548), and $C_{41}H_{42}$ (molecular weight 534).

Little or no published work is available for undecamantanes and higher molecular weight diamondoids. Undecamantane compounds have not been artificially synthesized or isolated and these higher diamondoids along with hexamantane, heptamantane, octamantane, nonamantane and decamantane compounds have been recently thought only to have a theoretical existence.[7] Academic chemists have primarily focused research on the interplay between physical and chemical properties in lower diamondoids such as adamantane, diamantane and triamantane. Adamantane and diamantane, for instance, have been studied to elucidate structure-activity relationships in carbocations and radicals.[3] Process engineers have directed efforts toward removing lower diamondoids from hydrocarbon gas streams.[2] These compounds cause problems during the production of natural gas by solidifying in pipes and other pieces of equipment.

The literature contains little information regarding practical applications of higher diamondoids and even less, if any, information regarding undecamantanes. This fact is probably due to extreme difficulties encountered in their isolation and due to failed synthesis attempts. Lin and Wilk, for example, discuss the possible presence of pentamantanes in a gas condensate and further postulate that hexamantane may also be present.[1] The researchers postulate the existence of these compounds contained within petroleum solely based on a mass spectrometric selected ion monitoring (SIM) and mass spectral fragmentation patterns. They did not, however, report the isolation of a single pentamantane or hexamantane nor mention heptamantane, octamantane, nonamantane, decamantane or undecamantane. Nor were they able to separate non-ionized components during their spectral analysis. McKervey et al. discuss an extremely low-yielding synthesis of anti-tetramantane.[3] The procedure involves complex starting materials and employs drastic reaction conditions (e.g., gas phase on platinum at 360° C.). Although one isomer of tetramantane, i.e. anti-, has been synthesized through a double homologation route, these syntheses are quite complex reactions with large organic molecules in the gas phase and have not led to the successful synthesis of other tetramantanes. Similar attempts using preferred ring starting materials in accordance with the homologation route, have likewise failed in the synthesis of pentamantanes. Likewise, attempts using carbocation rearrangement routes employing Lewis acid catalysts, useful in synthesizing triamantane and lower diamondoids have been unsuccessful in synthesizing other tetramantanes or pentamantanes. No attempt to synthesize or isolate undecamantanes has been reported.

Among other properties, diamondoids have by far the most thermodynamically stable structures of all possible hydrocarbons that possess their molecular formulas due to the fact that diamondoids have the same internal "crystalline lattice" structure as diamonds. It is well established that diamonds exhibit extremely high tensile strength, extremely low chemical reactivity, electrical resistivity greater than aluminum trioxide ($Al_2O_3$), excellent thermal conductivity, and superb optical properties.

In addition, based on theoretical considerations, the undecamantanes have sizes in the nanometer range and, in view of the properties noted above, the inventors contemplate that such compounds would have utility in micro- and molecular-electronics and nanotechnology applications. In particular, the rigidity, strength, stability, variety of structural forms and multiple attachment sites shown by these molecules makes possible accurate construction of robust, durable, precision devices with nanometer dimensions. The various undecamantanes are three-dimensional nanometer sized units showing different diamond lattice arrangements. This translates into a variety of rigid shapes and sizes for the undecamantane components. For example, [1212121212] undecamantane is rod shaped and [123(1,2)42143] undecamantane is somewhat pyramidal in structure. A variety of other shapes exist among the undecamantanes which may serve in applications which depend upon specific geometries. It has been estimated that MicroElectroMechanical Systems (MEMs) constructed out of diamond should last 10,000 times longer then current polysilicon MEMs, and diamond is chemically benign and would not promote allergic reactions in biomedical applications.[6] Again, the inventors contemplate that the various undecamantanes would have similar attractive properties. Furthermore, many of the undecamantanes would possess chirality, offering opportunities for making nanotechnology objects of great structural specificity and ones which have useful optical properties. Applications of these undecamantanes include molecular electronics, photonics devices and production of nanomechanical devices, and other materials.

Notwithstanding these advantages of undecamantanes, the art, as noted above, fails to provide for compositions comprising undecamantanes or for processes that would lead to these compositions. In view of the above, there is an ongoing need in the art to provide for compositions comprising one or more undecamantanes.

SUMMARY OF THE INVENTION

This invention is directed to novel compositions comprising one or more undecamantane components.

Accordingly, in one of its composition aspects, this invention is directed to a composition comprising one or more undecamantane components wherein said composition comprises at least about 25 weight percent undecamantane components based on the total weight of the diamondoids in the composition.

In another of its composition aspects, the compositions preferably comprise one or more undecamantane components wherein the undecamantane components make up from about 50 to 100 weight percent, preferably about 70 to 100 weight percent, more preferably about 90 to 100 weight percent and even more preferably about 95 to 100 weight percent of the total weight of the diamondoids in the compositions.

In another of its composition aspects, the compositions comprise at least about 10 weight percent and preferably at least about 20 weight percent of undecamantanes based on the total weight of the composition. Other compositions of this invention contain from 50 to 100 weight percent, 70 to 100 weight percent, 95 to 100 weight percent and 99 to 100 weight percent of undecamantanes based on the total weight of the composition.

In another of its composition aspects, the compositions preferably comprise from about 70 to 100 weight percent, more preferably from about 90 to 100 weight percent, even more preferably about 95 to 100 weight percent and most preferably from about 99 to 100 weight percent of a single undecamantane component, including isolated optical isomers thereof, based on the total weight of the composition.

Compositions are sufficiently enriched in undecamantane components the undecamantanes can form crystal structures. Accordingly, another aspect of this invention is directed to a composition comprising an undecamantane crystal. Since such undecamantane can co-crystallize, another aspect of this invention is directed to the co-crystals comprising crystals of at least two undecamantane components or a undecamantane component and another higher diamondoid component.

This invention is also directed to novel processes for the separation and isolation of undecamantane components into recoverable fractions from a feedstock containing one or more undecamantane components and nonundecamantane materials. These processes for recovering a composition enriched in undecamantane components entail removing at least a portion of the nonundecamantane materials which have a boiling point below the lowest boiling undecamantane component and utilizing a subsequent separation technique to recover undecamantane components from the resulting residue. Accordingly, this aspect is directed to processes which comprise:

a) selecting a feedstock comprising recoverable amounts of undecamantane components and nonundecamantane materials;

b) removing from the feedstock a sufficient amount of nonundecamantane materials that have boiling points below the boiling point of the lowest boiling point undecamantane component in the feedstock under conditions to form a treated feedstock enriched in undecamantane components which can be recovered;

c) recovering undecamantane components by separating said treated feedstock formed in b) above with one or more additional separation techniques selected from the group consisting of chromatographic techniques, thermal diffusion techniques, zone refining, progressive recrystallization and size separation techniques.

In a preferred embodiment, after the step recited in b) the undecamantane components in the treated feedstock can be thermally treated to pyrolyze at least a sufficient amount of nondiamondoid components therefrom under conditions to provide a thermally treated feedstock retaining recoverable amounts of undecamantane. Such a pyrolization step prior to step c) is useful for thermally degrading at least a portion of any materials remaining in the treated feedstock having a thermal stability lower than the undecamantane components in common hydrocarbonaceous feedstocks. This pyrolysis step can be carried out in step b) if desired.

BRIEF DESCRIPTION OF THE DRAWINGS

FIG. 1 illustrates the correlation of the structures of diamondoids to subunits of the diamond crystal lattice.

FIG. 10B illustrates the GC of Feedstock B atmospheric distillation fraction #7, which was used as feedstock in pyrolytic processing. FIG. 10A illustrates the GC of the product of the pyrolytic process.

FIG. 12A, shows the first column cuts containing two of the heptamantanes from Feedstock B.

FIG. 12B, shows the second column peaks isolated and sent to the traps. From this procedure pure heptamantanes were isolated (FIGS. 13–16), heptamantane #1, the first heptamantane to elute in our GCIMS assay, and heptamantane #2 which is the second to elute. This same methodology can be used to separate decamantanes using HPLC fractions (e.g. FIG. 11) as a starting material.

FIG. 25 illustrates an undecamanatane having more steric strain than FIG. 24.

DETAILED DESCRIPTION OF THE INVENTION

This invention is directed to undecamantane compositions comprising one or more undecamantanes and to compositions enriched in undecamantanes and higher boiling point diamondoids. However, prior to describing this invention in further detail, the following terms will first be defined.

Definitions

As used herein, the following terms have the following meanings.

Figure 1:
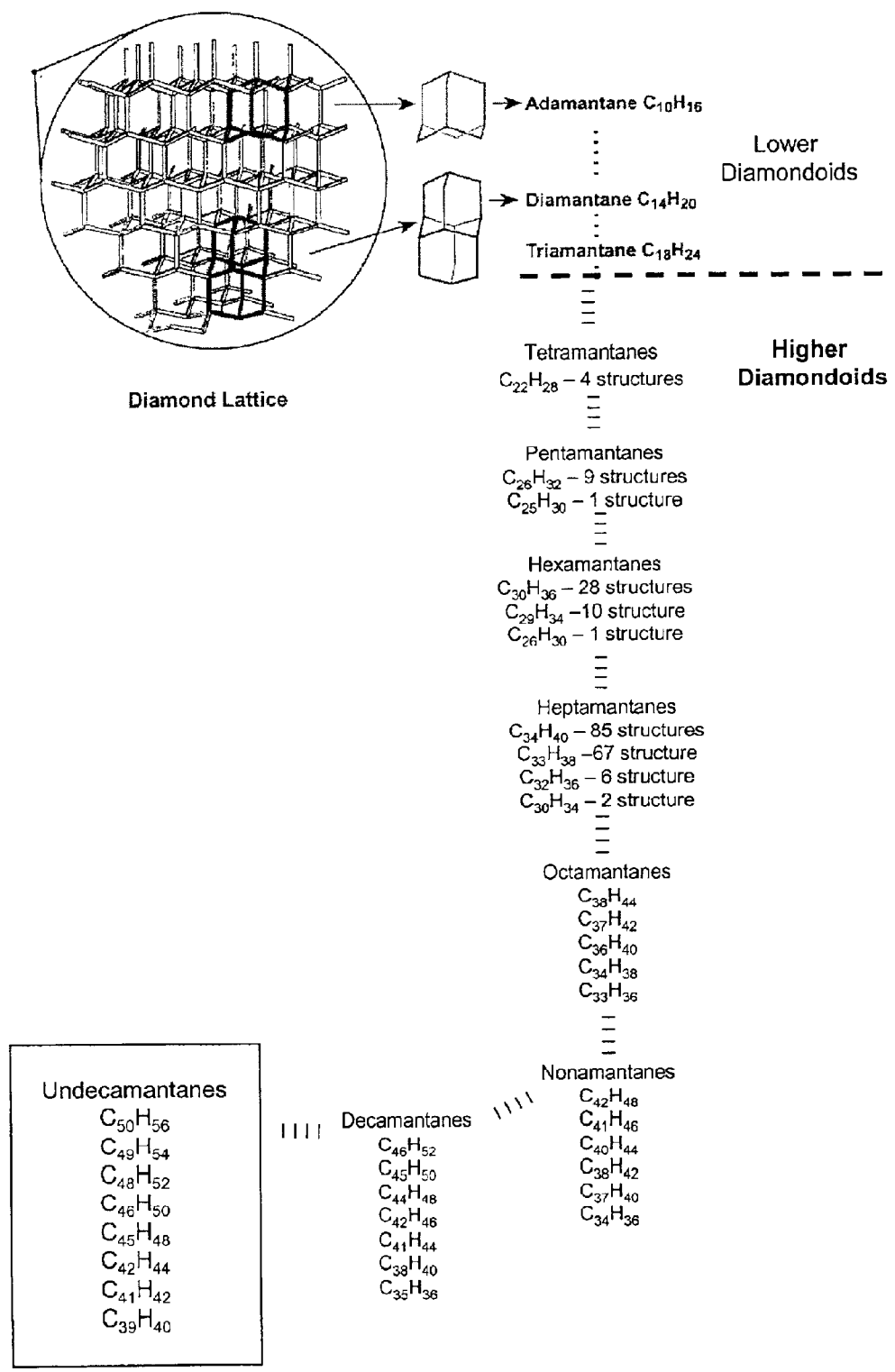
FIG. 1 illustrates the cage-shaped structure of diamondoids and their correlation to diamonds. Specifically.
Figure 2:
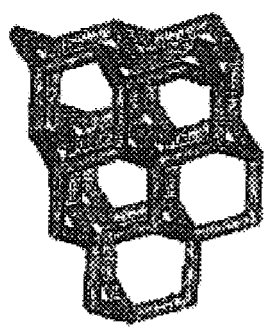
FIG. 2 illustrates the carbon framework example of a symmetrical and an enantiomeric undecamantane.
Figure 2:
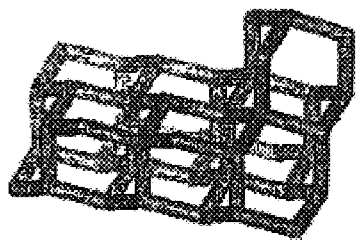
Figure 2:
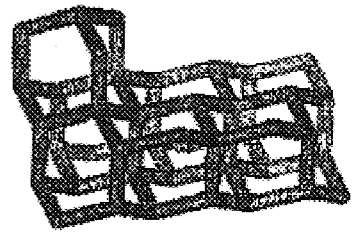

The term "diamondoids" refers to substituted and unsubstituted caged compounds of the adamantane series including adamantane, diamantane, triamantane, tetramantane, pentamantane, hexamantane, heptamantane, octamantane, nonamantane, decamantane, undecamantane, and the like and also including all isomers and stereoisomers thereof. The compounds have a "diamondoid" topology, which means their carbon atom arrangement is superimposable on a fragment of the diamond lattice (FIG. 1). Substituted diamondoids comprise from 1 to 10 and preferably 1 to 4 independently-selected alkyl substituents. Diamondoids include "lower diamondoids," "undecamantanes," "higher diamondoids" and "nonundecamanatane higher diamondoids" as these terms are defined herein The term "undecamantanes" refers to diamondoids that are by the face-fused undecamers of the adamantane series. Undecamantanes have eight possible formulae and weights: $C_{50}H_{56}$ (molecular weight 656), $C_{49}H_{54}$ (molecular weight 642), $C_{48}H_{52}$ (molecular weight 628), $C_{46}H_{50}$ (molecular weight 602), $C_{45}H_{48}$ (molecular weight 588), $C_{42}H_{44}$ (molecular weight 548) $C_{41}H_{42}$ and $C_{39}H_{40}$ (molecular weight 508). Each of the undecamantanes posseses a different three-dimensional structure. Undecamanatanes include substituted materials as described for diamondoids, generally.

The term "undecamantane components" refers to any single such substituted or unsubstitued undecamanatane, including optical isomers (enantiomers).

The term "lower diamondoids" or "adamantane, diamantane and triamantane components" refers to adamantane, diamantane and triamantane and any and/or all unsubstituted and substituted derivatives of adamantane, diamantane and triamantane. These lower diamondoid components show no isomers or chirality and are readily synthesized, distinguishing them from "higher diamondoids".

The term "higher diamondoids" refers to any and/or all substituted and unsubstituted tetramantane components; to any and/or all substituted and unsubstituted pentamantane components; to any and/or all substituted and unsubstituted hexamantane components; to any and/or all substituted and unsubstituted heptamantane components; to any and/or all substituted and unsubstituted octamantane components; to any and/or all substituted and unsubstituted nonamantane components; to any and/or all substituted and unsubstituted decamantane components; to any and/or all substituted and unsubstituted undecamantane components; as well as mixtures of the above as well as isomers and stereoisomers of tetramantane, pentamantane, hexamantane, heptamantane, octamantane, nonamantane, decamantane, and undecamantane. Those higher diamondoids which are not undecamantane components are referred to as "nonundecamantane higher diamondoids."

The term "feedstock" or "hydrocarbonaceous feedstock" refers to hydro-carbonaceous materials comprising recoverable amounts of one or more undecamantane components. Preferably, such feedstocks include gas condensates, refinery streams, and oil including oil derived from reservoir rocks, oil shale, tar sands, source rocks, and the like. Such feedstocks typically, but not necessarily, comprise lower diamondoids and other higher diamondoids as well as non-diamondoid components. The latter is typically characterized as comprising components having a boiling point both below and above undecamantane components, which show molecular weights ranging from 508 to 656, and therefore show a range of boiling points beginning at about 480° C. (atmospheric equivalent temperature). Typical feedstocks may also contain impurities such as sediment, metals including nickel and vanadium and other inorganics. They may also contain heteromolecules containing sulfur, nitrogen and the like. All of these materials which are not undecamantane components are referred to as "nonundecamantane materials" or "nonundecamantane components."

The term "enriched" when used to describe the state of purity of one or more undecamantane components refers to such materials at least partially separated from nonundecamantane materials, and in the case of "enriched" individual undecamantane components, from other undecamantane components so as to be at a concentration at least 25 and preferably at least 100 times as great as the concentration exhibited in a feedstock. Preferably "enriched" undecamantane or "enriched" undecamantane components make up at least 25%, especially at least 50% (i.e., 50–100%), more preferably at least 75% and yet more preferably at least 95% or even at least 99% by weight of the overall material in which they are present or in other words exhibit a weight purity of at least 25%, 50%, 75%–95% or 99% of such material.

The term "remove" or "removing" refers to processes for removal of nondiamondoid components and/or lower diamondoid components from the feedstock. Such processes include, by way of example only, size separation techniques, distillation, evaporation either under normal or reduced pressure, well head separators, chromatography, chemical extraction, crystallization and the like. For example, Chen, et al.[8] disclose distillation processes for removing adamantane, substituted adamantane, diamantane, substituted diamantane, and triamantane from a hydrocarbonaceous feedstock. Size separation techniques include membrane separations, molecular sieves, gel permeation, size exclusion chromatography and the like.

The terms "distillation" and "distilling" refer to atmospheric, reduced pressure distillation, and elevated pressure distillation conducted to concentrate undecamantane components by removal of nonundecamantane components from the feedstock based on boiling points. Unless otherwise specified, distillation temperatures are reported as atmospheric equivalents.

The terms "fractionation" and "fractionating" refer to processes in which materials in a mixture of materials are separated from each other such as by differential solubility, differential vapor pressure, differential chromatographic affinity and the like.

The terms "thermal degradation" and "pyrolytic processing" and the like refer to processes for treating a feedstock or a feedstock fraction at elevated temperature, to selectivity break down and/or pyrolyze at least a portion of nondiamondoid components in the feedstock or feedstock fraction.

The term "nondiamondoid components" refers to components of the feedstock that are not diamondoid in character wherein the term "diamondoid" is as defined herein.

The term "chromatography" refers to any of a number of well known chromatographic techniques including, by way of example only, column or gravity chromatography (either normal or reverse phase), gas chromatography, high performance liquid chromatography, and the like.

The term "alkyl" refers to straight and branched chain saturated aliphatic groups typically having from 1 to 20 carbon atoms, more preferably 1 to 6 atoms ("lower alkyls"), as well as cyclic saturated aliphatic groups typically having from 3 to 20 carbon atoms and preferably from 3 to 6 carbon atoms ("lower alkyls" as well). The terms "alkyl" and "lower alkyl" are exemplified by groups such as methyl, ethyl, propyl, butyl, isopropyl, isobutyl, sec-butyl, t-butyl, n-heptyl, octyl, cyclopropyl, cyclobutyl, cyclopentyl, cyclohexyl and the like.

Methodology

The compositions of this invention can be obtained from readily available starting materials using the following general methods and procedures. It will be appreciated that where typical or preferred process conditions (i.e., reaction temperatures, times, solvents, pressures, etc.) are given, other process conditions can also be used unless otherwise stated. Optimum reaction conditions may vary with feedstocks, but such conditions can be determined by one skilled in the art by routine optimization procedures.

Detailed methods for processing feedstocks to obtain higher diamondoid compositions are set forth in U.S. Provisional Patent Application No. 60/262,842 filed January 19, 2001; U.S. Provisional Patent Application No. 60/300,148 filed Jun. 21, 2001; U.S. Provisional Patent Application No. 60/307,063 filed Jul. 20, 2001; U.S. Provisional Patent Application No. 60/312,563 filed Aug. 15, 2001; U.S. Provisional Patent Application No. 60/317,546 filed Sep. 5, 2001, U.S. Provisional Patent Application No. 60/323,883 filed Sep. 20, 2001 and U.S. Provisional Patent Application Nos. 60/348,355 and 60/348,319 both filed Oct. 19, 2001, respectively; these applications are herein incorporated-by-reference in their entirety.

To obtain the undecamantane compositions described herein, a feedstock is selected such that said feedstock comprises recoverable amounts of undecamantane. Preferably, such feedstock comprises at least about 1 part per trillion of undecamantane components. It is understood, of course, that feedstocks having higher concentrations of undecamantanes facilitate recovery of these materials.

Preferred feedstocks include, for example, natural gas condensates and refinery streams having high concentrations of diamondoids. With regard to the latter, such refinery streams include hydrocarbonaceous streams recoverable from cracking processes, distillations, coking and the like. Particularly preferred feedstocks include feedstocks recovered from the Norphlet Formation in the Gulf of Mexico and from the LeDuc Formation in Canada.

The feedstocks used to obtain the compositions of this invention typically comprise nondiamondoid components having boiling points both below and above the lowest boiling point undecamantane component as well as one or more lower diamondoids and nonundecamantane higher diamondoids. A sufficient amount of these contaminants is removed from the feedstocks to provide treated feedstocks from which the undecamantane components can be recovered.

The removal of contaminants including lower diamondoids, nonundecamantane higher diamondoids and/or hydrocarbonaceous non-diamondoid material include, by way of example only, size separation techniques such as membranes, molecular sieves, etc., evaporation and thermal separators either under normal or reduced pressures, extractors, electrostatic separators, crystallization, chromatography, well head separators, and the like. A preferred separation method typically includes distillation of the feedstock to remove nondiamondoid components as well as nonundecamantanes having boiling points less than that of the lowest boiling point undecamantane component. Temperature profiles for distillation runs and the resulting distillation cuts can be determined on the basis of the undecamantane of interest. Preferably, the feedstock is distilled to provide cuts above and below about 335° C., atmospheric equivalent boiling point, more preferably, above and below about 345° C. atmospheric equivalent boiling point and more preferably, above and below about 370° C. atmospheric equivalent boiling point. In each instance, the lower cuts, which are enriched in lower diamondoids and low boiling point nondiamondoid components, are discarded. Distillation can be operated to provide several cuts in the temperature range of interest to provide the initial concentration of the identified higher diamondoid. The cuts, which are enriched in undecamantanes or the particular undecamantane component of interest, are retained and may require further purification. For recovery of undecamantanes, the preferred distillation cuts are taken at temperatures of from 450° to about 600° C., preferably from 480° to about 585° C. (atmospheric equivalent boiling point). Additional temperature refinements will allow for higher purity cuts for the undecamantane of interest. Other methods for the removal of contaminants and further purification of an enriched undecamantane fraction can additionally include the following nonlimiting examples: size separation techniques, evaporation either under normal or reduced pressure, sublimation, crystallization, chromatography, well head separators, flash distillation, fixed and fluid bed reactors, reduced pressure and the like.

The contaminant removal may also include a thermal degradation step either prior or subsequent to distillation. Thermal degradation is an effective method to remove hydrocarbonaceous, nondiamondoid components from the feedstock. It is effected by heating the feedstock under vacuum conditions or in an inert atmosphere, at a reactor temperature of at least about 390° C. (most preferably about 410 to about 450° C.). The specific conditions employed are selected such that recoverable amounts of undecamantane components are retained in the feedstock. The selection of such conditions is well within the skill of the art. Preferably, pyrolysis is continued for a sufficient period of time and at a sufficiently high enough temperature to thermally degrade at least about 10% by weight of the nondiamondoids components of the feed material prior to pyrolysis. More preferably at least 50% and even more preferably at least 90% of the nondiamondoids are thermally degraded.

Thermal degradation, while a preferred embodiment, is not always necessary to facilitate the recovery, isolation or purification of the undecamantane components. Other separation methods may allow for the concentration of these undecamantane components to be sufficiently high in certain feedstocks that direct purification methods such as chromatography including preparative gas chromatography and high performance liquid chromatography, crystallization, fractional sublimation may be used to isolate undecamantane components.

Even after distillation or thermal degradation/distillation, further purification of the undecamantane components may be desired to provide the compositions of this invention. One may use purification techniques such as chromatography, crystallization, thermal diffusion techniques, zone refining, progressive recrystalization, size separation and the like. For instance, in one process, the treatment feedstock is subjected to one or more of the following additional procedures: 1) gravity column chromatography using silver nitrate impregnated silica gel; 2) one or multiple column high performance liquid chromatography and/or two-column preparative capillary gas chromatography to isolate the undecamantanes; 3) crystallization to provide crystals of the highly concentrated undecamantanes.

An alternative process is to use liquid chromatography including high performance liquid chromatography followed by gas chromatography to isolate the undecamantanes of interest.

Further processing using these methods allow for more refined separations which can lead to a pure undecamantane component. Enantioselective (chiral) stationary phases have been applied in chromatographic methods to effectuate further separations. High performance liquid chromatography methods also offer the possibility of using chiral solvents or additives to achieve resolution of enantiomers.

For example, separation of enantiomeric forms of the undecamantanes can be achieved using several approaches. One such approach is spontaneous crystallization with resolution and mechanical separation. This approach to enantiomer resolution can be enhanced by preparation of derivatives or by the use of additives, chiral solvents, or various types of seed crystals. The presence of conglomerate crystals supports the effectiveness of this approach. Another resolution option is chemical separation under kinetic or thermodynamic control. Other suitable processes for enantiomers resolution include chiral separations, which can be preformed using a gas chromatographic (GC) see "Chiral Chromatography", T. E. Beesley, et. al, Wiley, Johnson & Sons, January 1998, incorporated herein by reference, by high performance liquid chromatographic (HPLC) and by supercritical fluid chromatographic (SFC) techniques, see Supercritical fluids in Chromatography and Extraction", R. M. Smith, Elsevier Science, December 1997, incorporated herein by reference.

Compositions

This invention is directed to compositions comprising one or more undecamantane components wherein said compositions comprise at least about 25 weight percent undecamantane components based on the total weight of the diamondoids in the compositions. The compositions preferably comprise from about 50 to 100 weight percent, preferably about 70 to about 100 weight percent, more preferably about 90 to 100 weight percent and even more preferably about 95 to 100 weight percent undecamantane components based on the total weight of the diamondoids in the composition.

Such undecamantane-enriched compositions are obtained through the series of unit operations described above which can be used to concentrate undecamantanes to at least 25 times and more preferably at least 100 times the levels at which they occur in readily-available feedstocks. The total weight percent of undecamantane components in the compositions is preferably at least 10% by weight based upon the total weight of the composition. In a more preferred aspect the total weight percent of undecamantane components is from 50 to 100 weight percent, more preferably 70 to 100 weight percent and even more preferably 95 or 99 to 100 weight percent based upon the total weight percent of the composition.

In other aspects, the compositions comprise an enriched individual undecamantane component such that they contain from 70 to 100 weight percent, more preferably from 90 to 100 weight percent, even more preferably from 95 to 100 weight percent and most preferably from 99 to 100 weight percent of a single undecamantane component including isolated optical isomers thereof.

Figure 20:
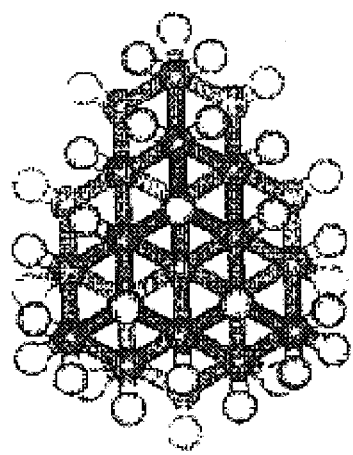
FIGS. 20–22 illustrate an example ball and stick, stick with hydrogen removed, and CPK model of a molecular formula $C_{39}H_{40}$ (molecular weight 508) undecamantane.
Figure 20:
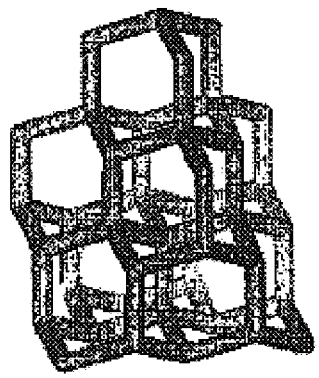
Figure 20:
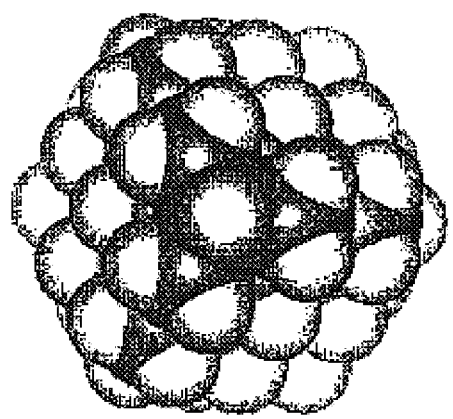
Figure 21:
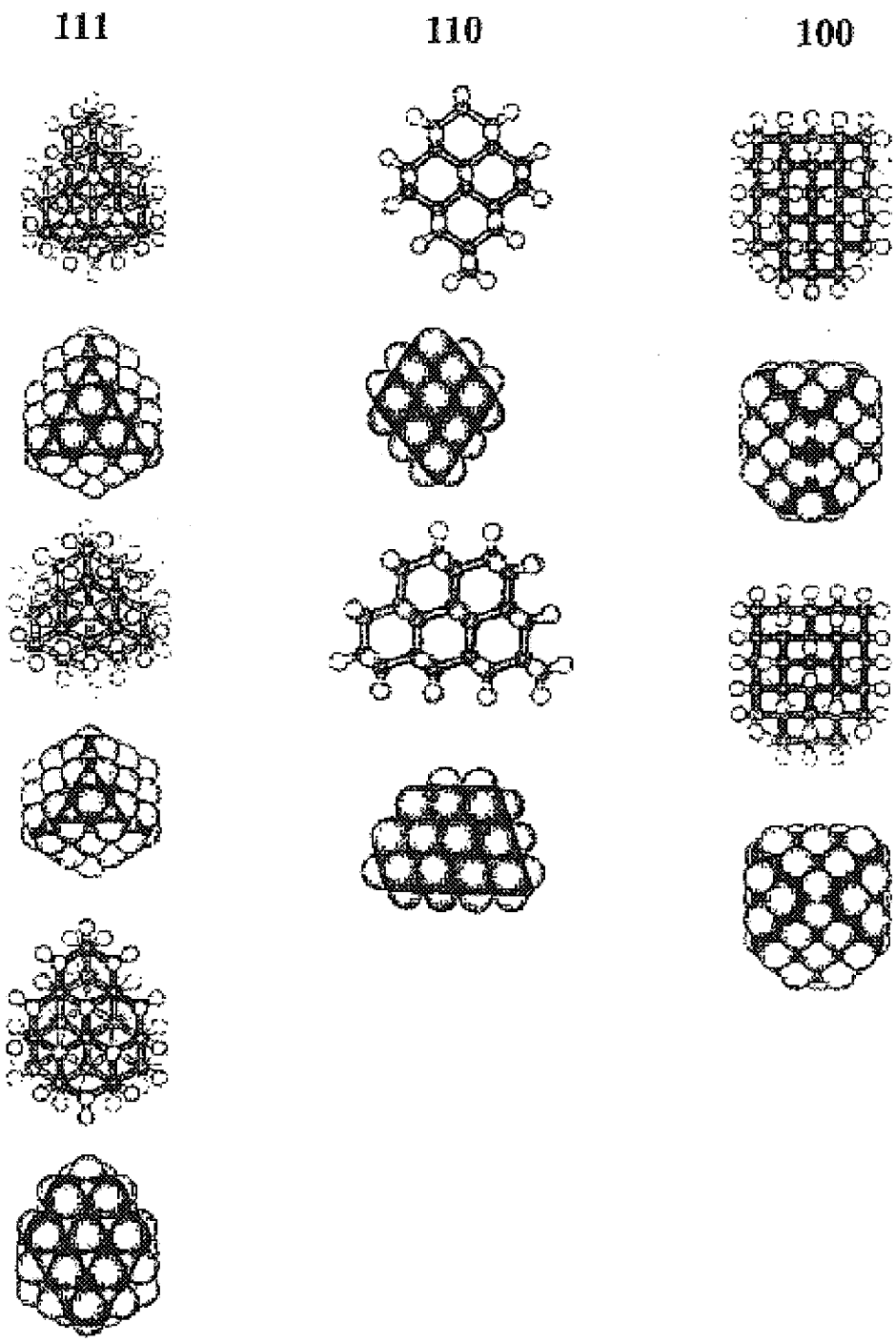
Figure 22:
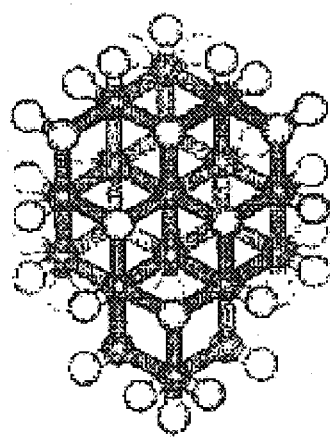
Figure 22:
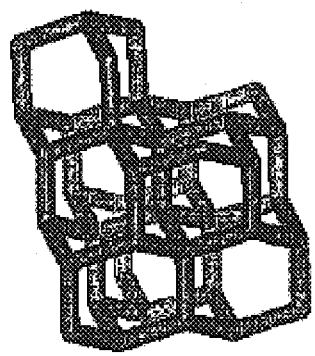
Figure 22:
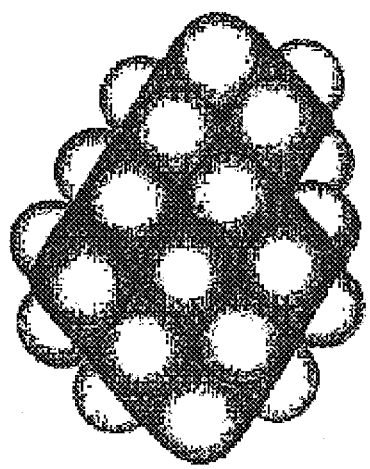

In a most preferred embodiment, the composition aspects of this invention are directed to the undecamantanes having the molecular formula $C_{39}H_{40}$ (molecular weight 508). More preferably the single mol. weight 508 undecamantane with the structures and lattice planes shown in FIGS. 20–22, which also names a preferred mol. weight 508 compound as [123(1,2)42143] undecamanatane using the convention as outlined in Balaban et al.[7] Other undecamanatanes can likewise be named. This particular [123(1,2)42143] (molecular weight 508) undecamantane is unique when compared to the other undecamantanes because it is one of the two most condensed undecamantes and has the least steric strain of the two. While it is one of the two possible molecular weight 508 undecamantanes it is evident from observing structural models (for example see FIGS. 20–22) and considering steric strain that its structure is the most stable mol. weight 508 undecamantane and accordingly, compositions containing [123(1,2)42143] undecamantane are a preferred embodiment.

Figure 23:
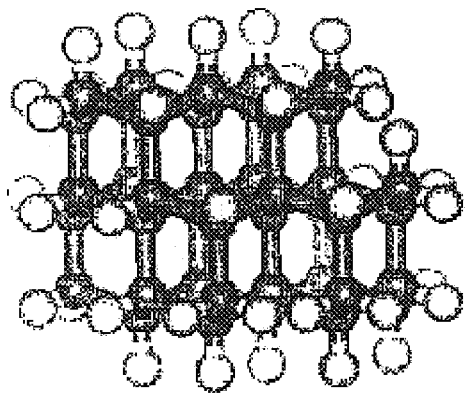
FIG. 23 illustrate an example ball and stick, stick with hydrogen removed, and CPK model of a molecular formula $C_{41}H_{42}$ (molecular weight 534 undecamantane.
Figure 23:
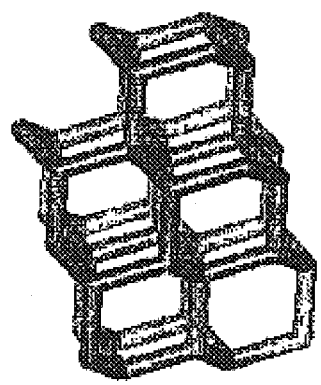
Figure 23:
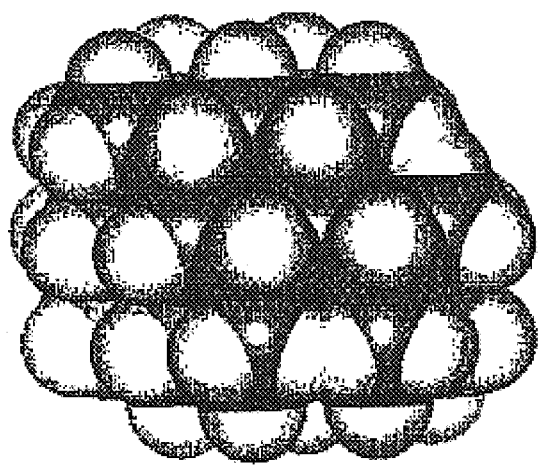
Figure 24:
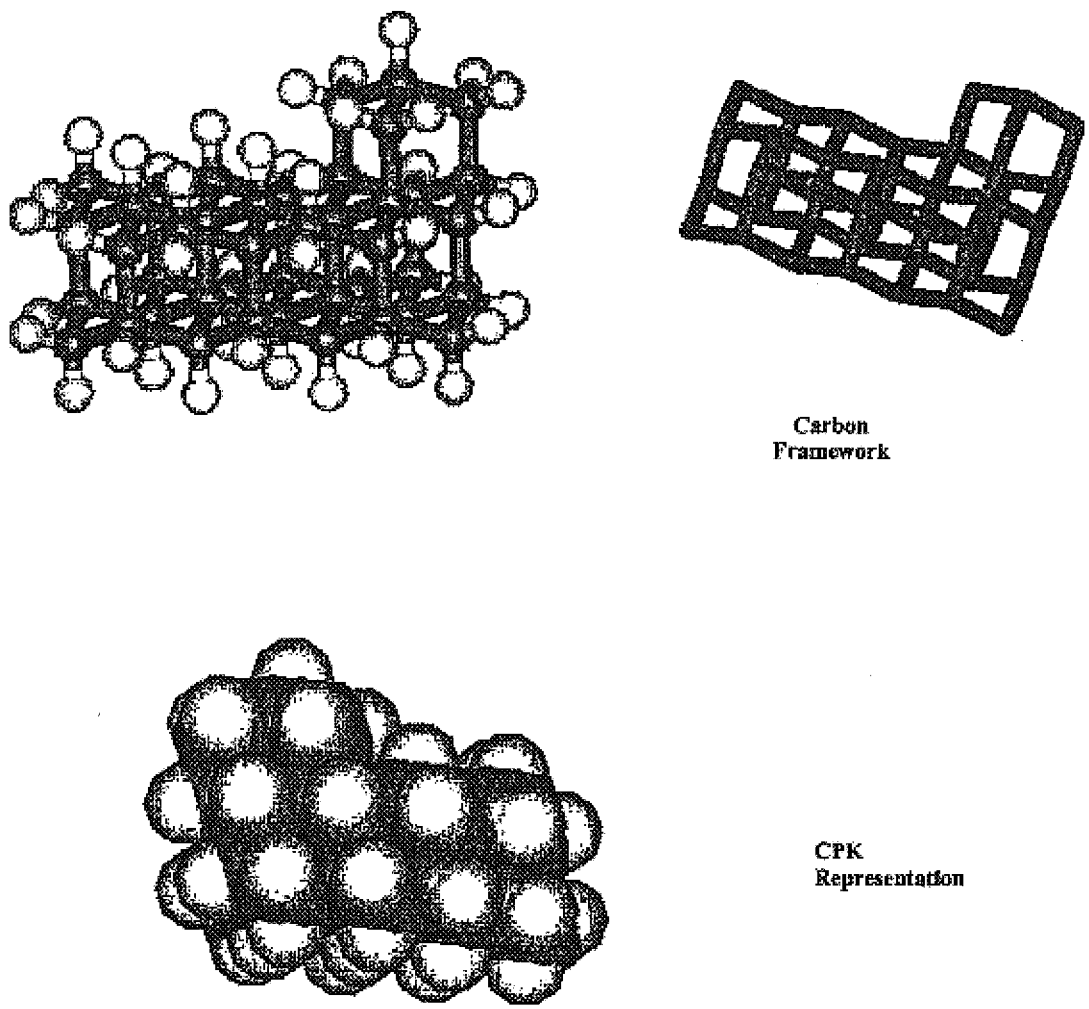
FIGS. 24–25 illustrate an example ball and stick, stick with hydrogen removed, and CPK model of a molecular formula $C_{42}H_{44}$ (molecular weight 548) undecamantane.
Figure 25:
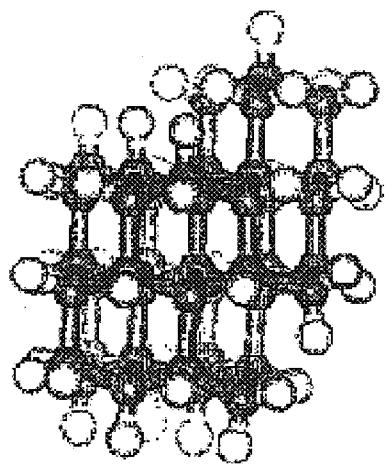
Figure 25:
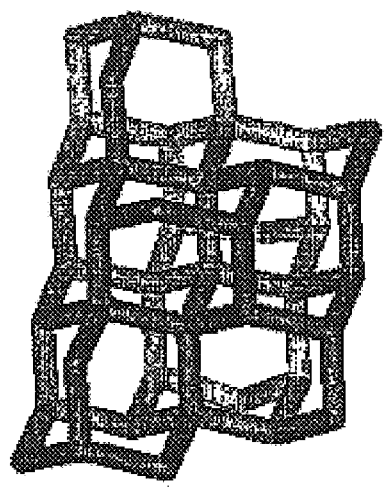
Figure 25:
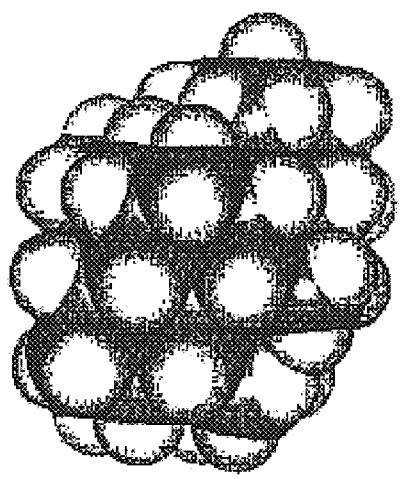
Figure 26:
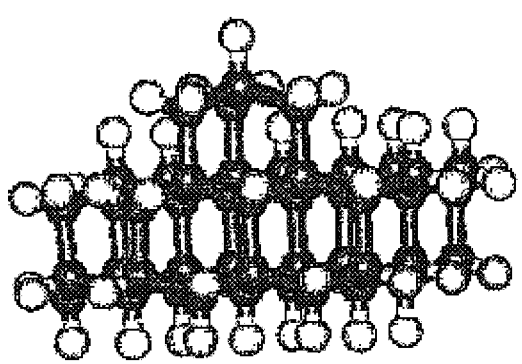
FIG. 26 illustrate an example ball and stick, stick with hydrogen removed, and CPK model of a molecular formula $C_{45}H_{48}$ (molecular weight 588) undecamantane.
Figure 26:
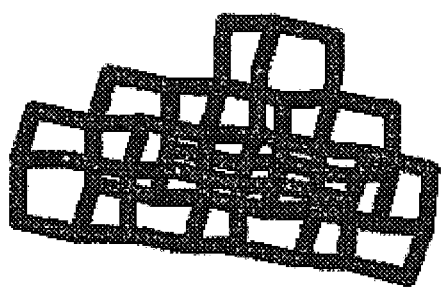
Figure 26:
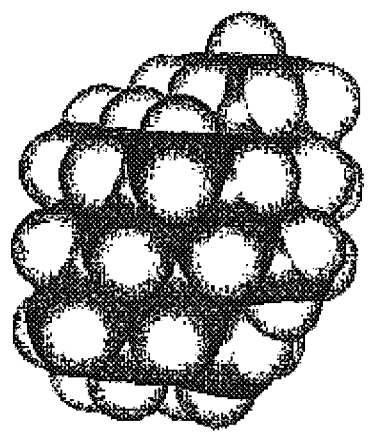
Figure 27:
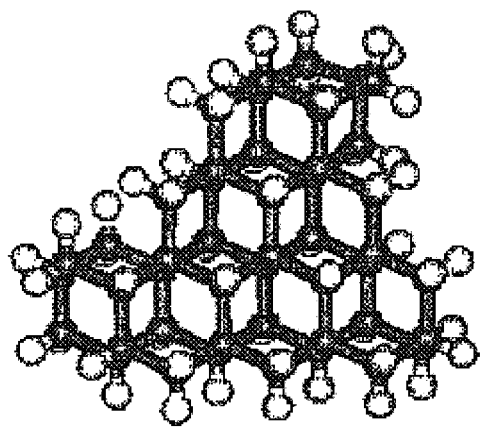
FIG. 27 illustrate an example ball and stick, stick with hydrogen removed, and CPK model of a molecular formula $C_{46}H_{50}$ (molecular weight 602) decamantane.
Figure 27:
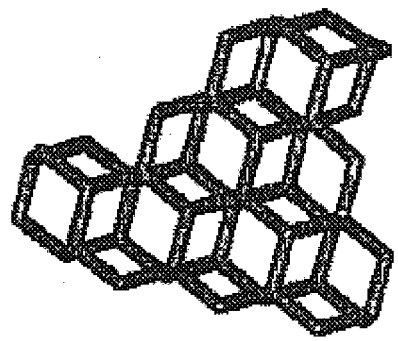
Figure 27:
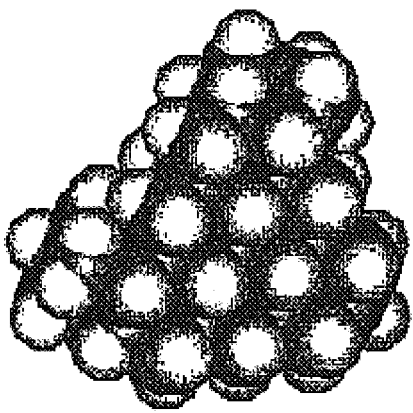
Figure 28:
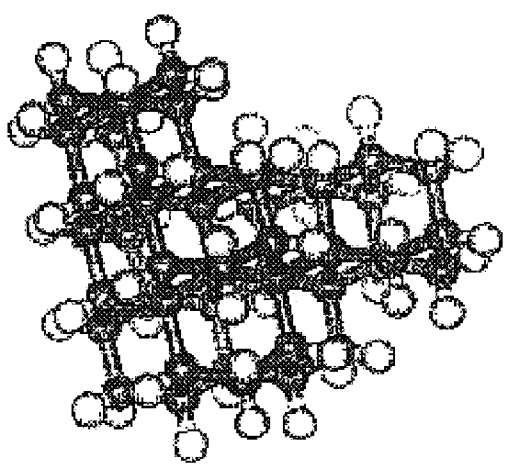
FIG. 28 illustrate an example ball and stick, stick with hydrogen removed, and CPK model of a molecular formula $C_{48}H_{52}$ (molecular weight 628) undecamantane.
Figure 28:
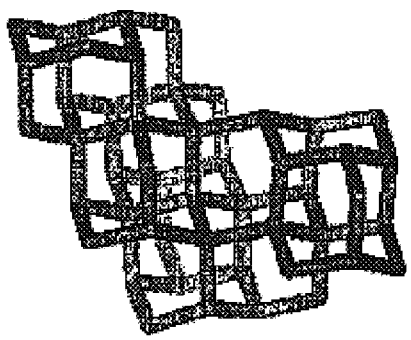
Figure 28:
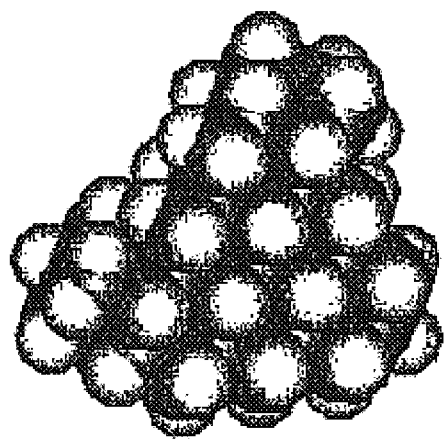
Figure 29:
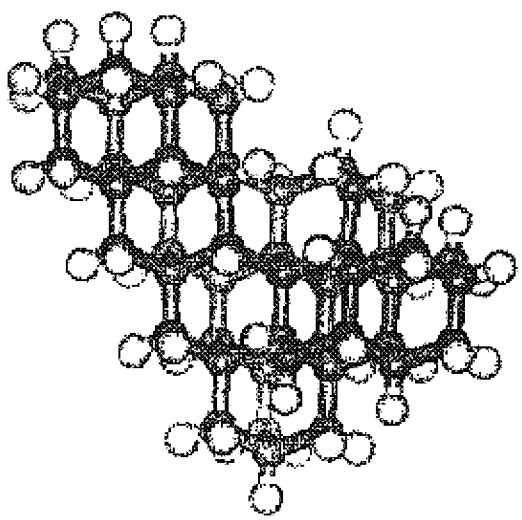
FIG. 29 illustrate an example ball and stick, stick with hydrogen removed, and CPK model of a molecular formula $C_{49}H_{54}$ (molecular weight 642) undecamantane.
Figure 29:
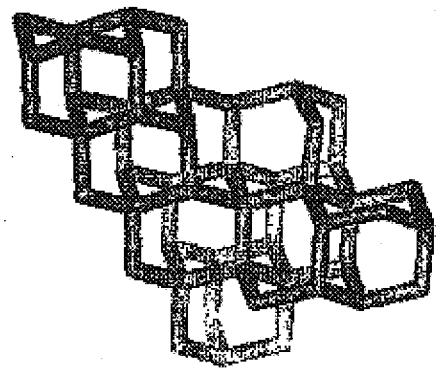
Figure 29:
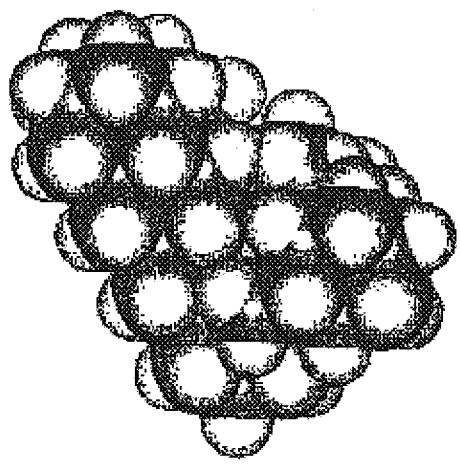
Figure 30:
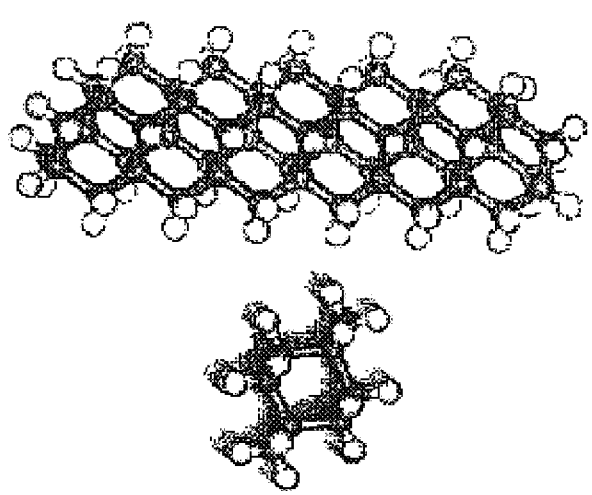
FIG. 30 illustrate an example ball and stick, stick with hydrogen removed, and CPK model of a molecular formula $C_{50}H_{56}$ (molecular weight 656) undecamantane.
Figure 30:
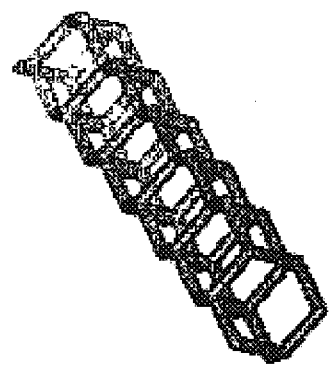
Figure 30:
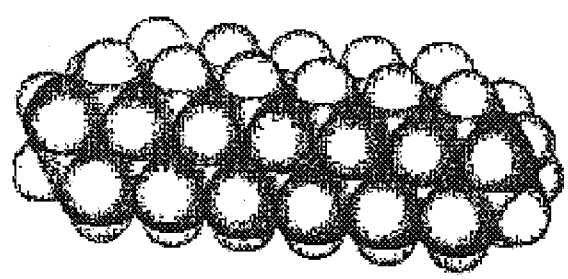

In another preferred aspect, the compositions are directed to the undecamantanes having the molecular formula $C_{50}H_{56}$ (molecular weight 656) and having the molecular formula $C_{46}H_{50}$ (molecular weight 602), with examples structures shown in FIGS. 30 and 27, respectively. As is apparent from studying their molecular structures and special geometries that these undecamantanes have relatively low steric strain. Other aspects of the diamondoid compositions are directed to the undecamantanes represented by the FIGS. 23–30; with example structures of the various molecular weights shown in: FIG. 29 having the molecular formula $C_{49}H_{54}$ (molecular weight 642), FIG. 28 having the molecular formula $C_{48}H_{52}$ (molecular weight 628), FIG. 26 having the molecular formula $C_{45}H_{48}$ (molecular weight 588), FIG. 25 having the molecular formula $C_{42}H_{44}$ (molecular weight 548), and FIG. 23 having the molecular formula $C_{41}H_{42}$ (molecular weight 534). The preferred groups within the above referenced molecular weights are the undecamantanes represented by one or more of the molecular weights 508, 602 and 656. Also within this invention are mixtures of one or more of these molecular weights. The composition aspects of this invention are directed to compositions comprising one or more of these undecamantanes including mixtures thereof, compositions enriched in undecamantanes, as well as processes for recovering said compositions enriched in such undecamantane components.

When such compositions are sufficiently enriched in undecamantane component,s the undecamantanes can form crystal structures. Accordingly, another aspect of this invention is directed to a composition comprising an undecamantane crystal. Also the undecamantane can be a substituted undecamantane component as described herein. Since such undecamantane components can co-crystallize, another aspect of this invention is directed to the co-crystals comprising crystals of at least two undecamantane components. Undecamantanes can also co-crystallize with other higher diamondoids, such as nonamantane components.

Another aspect of this invention is directed to enrichment and/or isolation of substituted undecamantane components. Within the preferred feedstock used substituted undecamantanes are present. These natural occurring substituted undecamantanes would have similar properties to the unsubstituted undecamantanes described herein. Alternatively, these components may act as useful intermediates in various undecamantane applications or can be de-alkylated to yield the corresponding unsubstituted undecamantane. Accordingly, the methods devised above for the isolation of individual undecamantanes also can yield individual substituted undecamantanes. Therefore, this invention is also directed to enriched as well as isolated compositions comprising these substituted undecamantane components. Therefore, another compositional aspect of this invention is directed to compositions which preferably comprise one or more substituted undecamantanes from about 25 to 100 weight percent, preferably about 50 to 100 weight percent, more preferably about 70 to 100 weight percent, more preferably about 90 to 100 weight percent and even more preferably about 95 to 100 weight percent undecamantane components based on the total weight of the diamondoids in the composition. Preferred substituted undecamantanes contain from 1 to 10 substituents, and more preferably 1 to 4 substituents, independently selected from the group consisting of alkyl moieties. More preferably the alkyl group is selected from methyl, ethyl, propyl, butyl, iso-propyl, iso-butyl, sec-butyl, tert-butyl. The most preferred substituted undecamantanes are methyl, ethyl, dimethyl, trimethyl and tetramethyl groups.

Utility

These undecamantane containing compositions are useful in micro- and molecular-electronics and nanotechnology applications. In particular, the rigidity, strength, stability, variety of structural forms and multiple attachment sites shown by undecamantanes makes possible accurate construction of robust, durable, precision devices with nanometer dimensions. These special structural characteristics set these compounds apart from acyclic molecules, from condensed ring systems and even from bridged ring counterparts. The great stability, nanometer size, variable yet rigid 3-dimensional geometries, well defined distances for places of attachment and nonplanar bridgeheads lead to their unique features. Such features make these undecarnantane compounds and compositions useful in nanotechnogy applications. In recent years there has been a rapidly rising interest in synthesizing large assemblies of organic molecules that might be able to serve as scaffolding structures in efforts to construct molecular objects of nanometer sized dimensions. Due to rigidity and special geometries of the undecamantane components, it is expected that molecular aggregates and molecular building blocks comprising them will enable the construction and synthesis of an unprecedented array of desirable materials and may find applications in molecular electronic and computing devices, small machines such as molecular robotics and self replicated manufacturing systems. Alternatively, they can be used simply as novel materials with special chemical, optical, electrical and thermal conductivity properties for coatings, film layering, and other applications taking advantage of the diamond-like properties, etc.

In addition, undecamantane-containing compositions can also be used in a high quality lubricant which exhibits a high Viscosity Index and a very low pour point.[4] When so employed, these lubricants comprise from about 0.1 to 10 weight percent undecamantanes.

Additionally, these undecamantane containing compositions can be used as high density fuels in the manner described by Chung, et al.[5], incorporated herein by reference.

The following examples are offered to illustrate this invention and are not to be construed in any way as limiting the scope of this invention. Unless otherwise stated, all temperatures are in degrees Celsius.

As used herein and in the Figures, the following abbreviations have the following meanings. Any abbreviation not defined below has its generally accepted meaning.

| | |
|---|---|
| API = | American Petroleum Institute |
| ATM EQV = | atmospheric equivalent |
| EOR Traps = | end of run traps |
| FID = | flame ionization detector |
| G = | grams |
| GC = | gas chromatography |
| GC/MS = | gas chromatography/mass spectroscopy |
| HPLC = | high performance liquid chromatography |
| HYD RDG = | hydrometer reading |
| MIN = | minute |
| ML = | milliliters |
| ODS = | octadecylsilane |
| pA = | pico amps |
| ppb = | parts per billion |
| RI = | refractive index |
| SFC = | super critical fluid chromatography |
| SIM DIS = | simulated distillation |
| ST = | start |
| TIC = | total ion current |
| VLT = | vapor line temperature |
| VOL PCT = | volume percent |
| WT PCT = | weight percent |

EXAMPLES

Example 1

Enrichment of Undecamantane Components

The purpose of this example is to demonstrate procedures for the isolation of undecamantane components. These procedures employed Feedstock B and a pyrolysis step, however this procedure could be facilitated using other materials, such as Feedstock A, and without the pyrolysis step. After removal of lower boiling point nonundecamantane components (including some lower diamondoids and tetramantanes from the feedstock by distillation), the undecamantane components in this example were recovered by chromatography and crystallization. The distillation preferably can be operated to provide specific cuts, thus removing both lower and higher boiling point components, leaving only components within a desired boiling point range.

Figure 3:
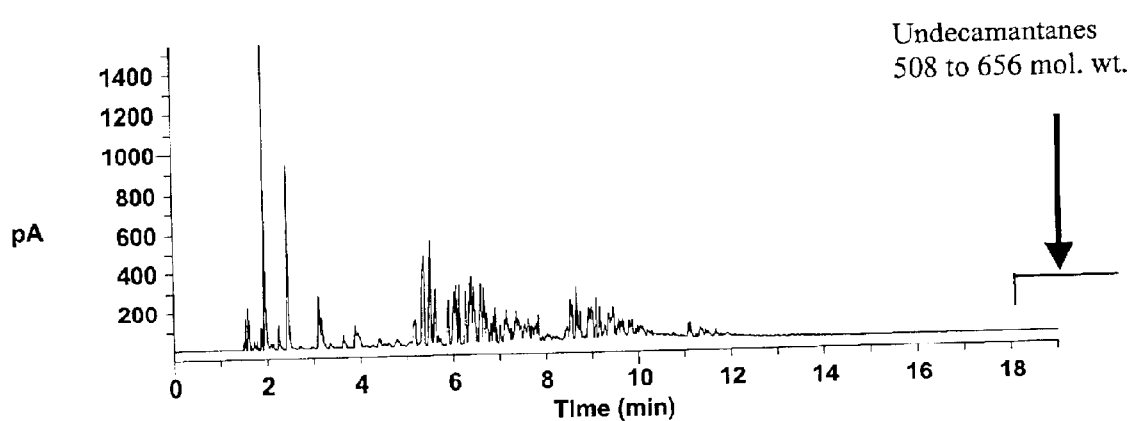
FIG. 3 illustrates the gas chromatogram of a gas condensate feedstock; one of the original feedstocks used in the Examples (Feedstock A). Undecamantanes are present at low concentrations.
Figure 4:
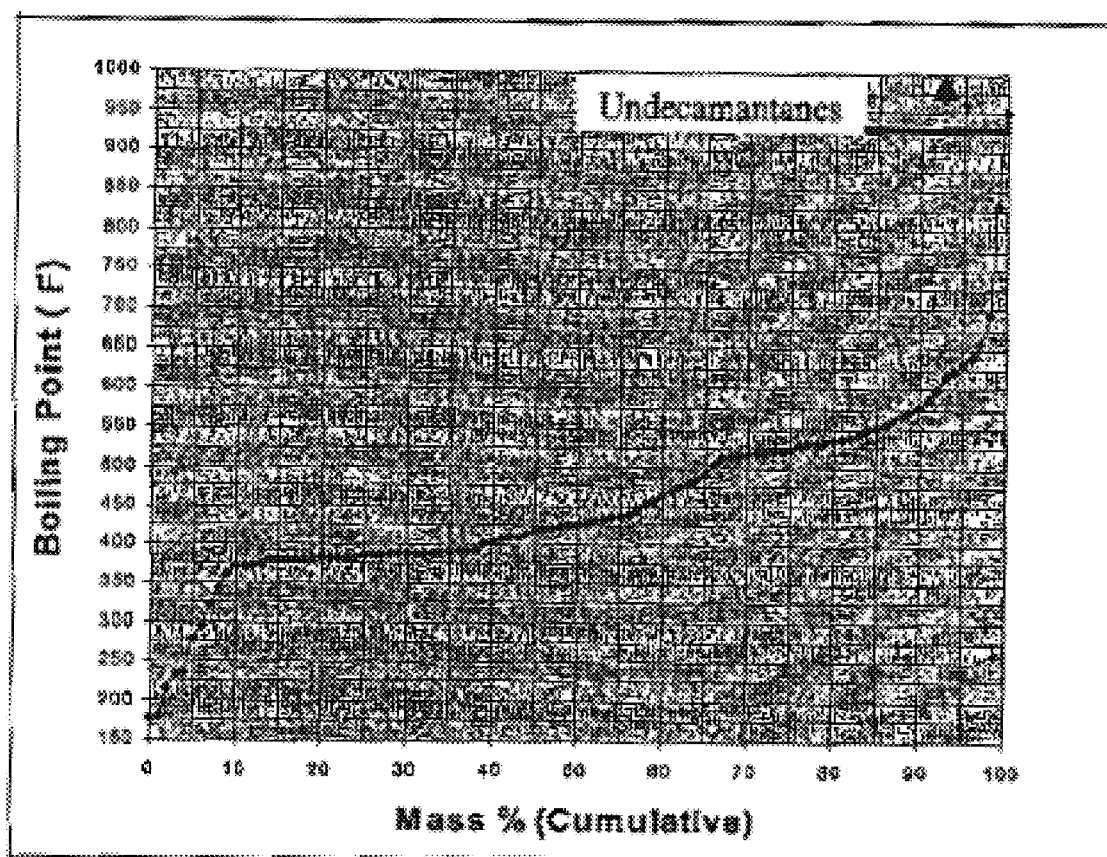
FIG. 4 illustrates a simulated distillation profile of a gas condensate feedstock containing petroleum byproducts used in the Examples (Feedstock B). Boiling points depicted are atmospheric equivalents. Undecamantanes were found in the atmospheric residue (650° F.+) of Feedstock B.

Step 1:

Suitable starting materials were obtained. These materials included a gas condensate, Feedstock A (a gas chromatogram of this material is depicted in FIG. 3), and a gas-condensate containing petroleum byproducts Feedstock B (a high temperature simulated distillation profile of this type of material is depicted in FIG. 4). Although other condensates, petroleums, or refinery cuts and products could have been used, these two materials were chosen due to their high concentration of higher diamondoids (0.3 weight percent), as determined by GC and GC/MS. Both feedstocks were light colored and had API gravities between 19 and 20° API.

Step 2:

Samples from Feedstocks A and B were distilled into a number of fractions based on boiling points to separate the lower boiling point components (nondiamondoids and lower diamondoids) and to further concentrate and enrich undecamantanes in various fractions. The yields of atmospheric distillate fractions of two separate samples of Feedstock B are shown in Table 1, below and are contrasted to the simulated distillation yields calculated for that feedstock. As seen from Table 1, the simulation data are in agreement with the distillation data.

TABLE 1

Yields of Atmospheric Distillation Fractions from Two Separate Runs of Feedstock B

| Cut (° F.) | Sim Dis Est.'d Yields (Wt %) | Feedstock B (Run 2) Yields (Wt %) | Difference |
|---|---|---|---|
| To 349 | 8.0 | 7.6 | 0.4 |
| 349 to 491 | 57.0 | 57.7 | −0.7 |
| 491 to 643 | 31.0 | 30.6 | 0.4 |
| 643 and higher | 4.0 | 4.1 | −0.1 |

| Cut (° F.) | Sim Dis Est.'d Yields (Wt %) | Feedstock B (Run 1) Yields (Wt %) | Difference |
|---|---|---|---|
| To 477 | 63.2 | 59.3 | 3.9 |
| 477 to 515 | 4.8 | 7.3 | −2.5 |
| 515 to 649 | 28.5 | 31.2 | −2.7 |
| 649 and higher | 3.5 | 2.1 | 1.4 |

Figure 5:
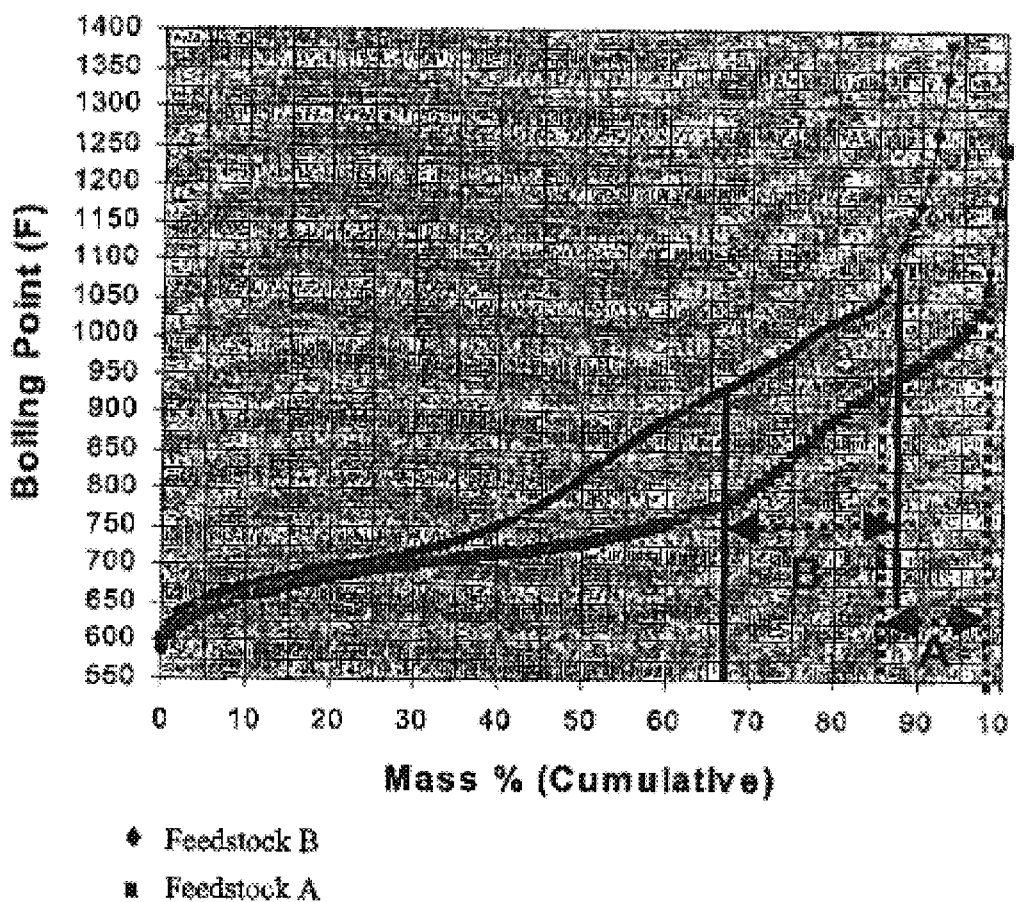
FIG. 5 illustrates a high temperature simulated distillation profile of atmospheric residue of diamondoid rich gas condensates; Feedstock A and Feedstock B. This Figure also illustrates the n-paraffin carbon number atmospheric equivalent boiling points. Labels A and B show the portions of each feedstock which contain the undecamantanes.

The higher diamondoid-containing atmospheric residue fraction from Feedstock B was in the 2 to 4 weight percent range as shown in Table 1. FIG. 5 compares a high-temperature simulated distillation profile of the atmospheric residue of the gas condensates, Feedstock A and Feedstock B. Additionally outlined is the identified location and size of the undecamantane-containing fractions. In terms of atmospheric equivalent boiling points, the undecamantane components boil predominately within the range of 400° F. to about 675° F. with a large portion within the range of 500° F. to about 590° F. Decamantanes also occur within the lower boiling point undecamantane fractions. The lower mass percent shown for the undecamantane-containing fractions of Feedstock B, as compared to Feedstock A was due to nondiamondoid materials in Feedstock B. The nondiamondoid material can be removed by subsequent processes such as pyrolysis.

A sample of gas condensate, Feedstock A was distilled into 38 fractions to remove lower diamondoids and concentrate higher diamondoids including undecamantanes. The residue left after vacuum distillation Fraction 38 predominantly boiled in the 750° F.+range (atmospheric equivalent). The boiling points of these fractions are given as atmospheric equivalent temperatures, however, the actual distillation can occur at other pressures and corresponding temperatures.

Figure 6:
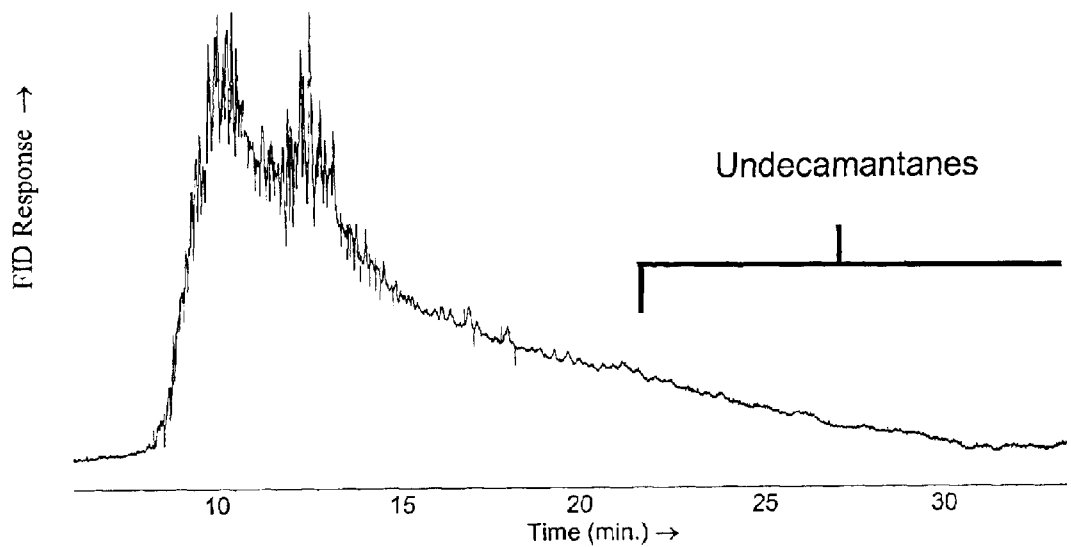
FIG. 6 illustrates gas chromatographic profiles of vacuum distillate residue containing undecamantanes and higher diamondoids from a gas condensate, Feedstock A.
Figure 7:
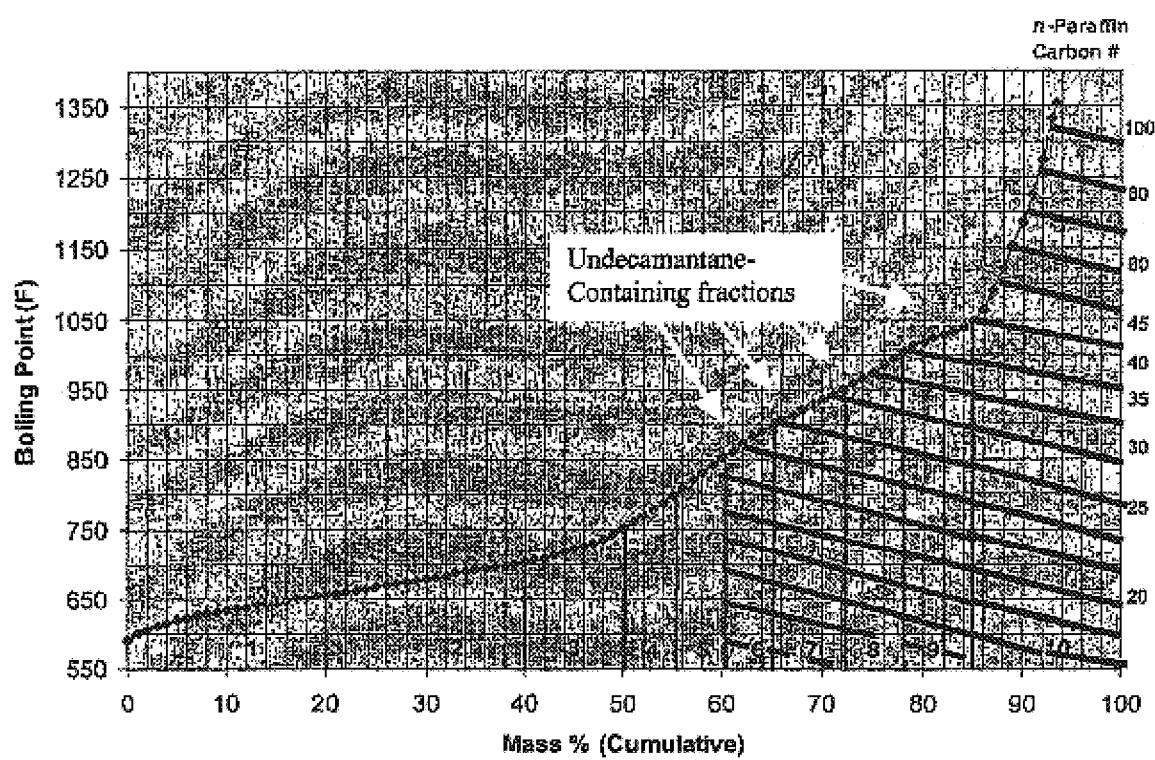
FIG. 7 illustrates a high temperature simulated distillation profile of Feedstock B using the atmospheric distillation 650° F.+bottoms as feedstock. This FIG. also illustrates the targeted cut points (1–10) for higher diamondoid isolations. Undecamantanes are contained primarily in distillate fractions 6 through 10.
Figure 8:
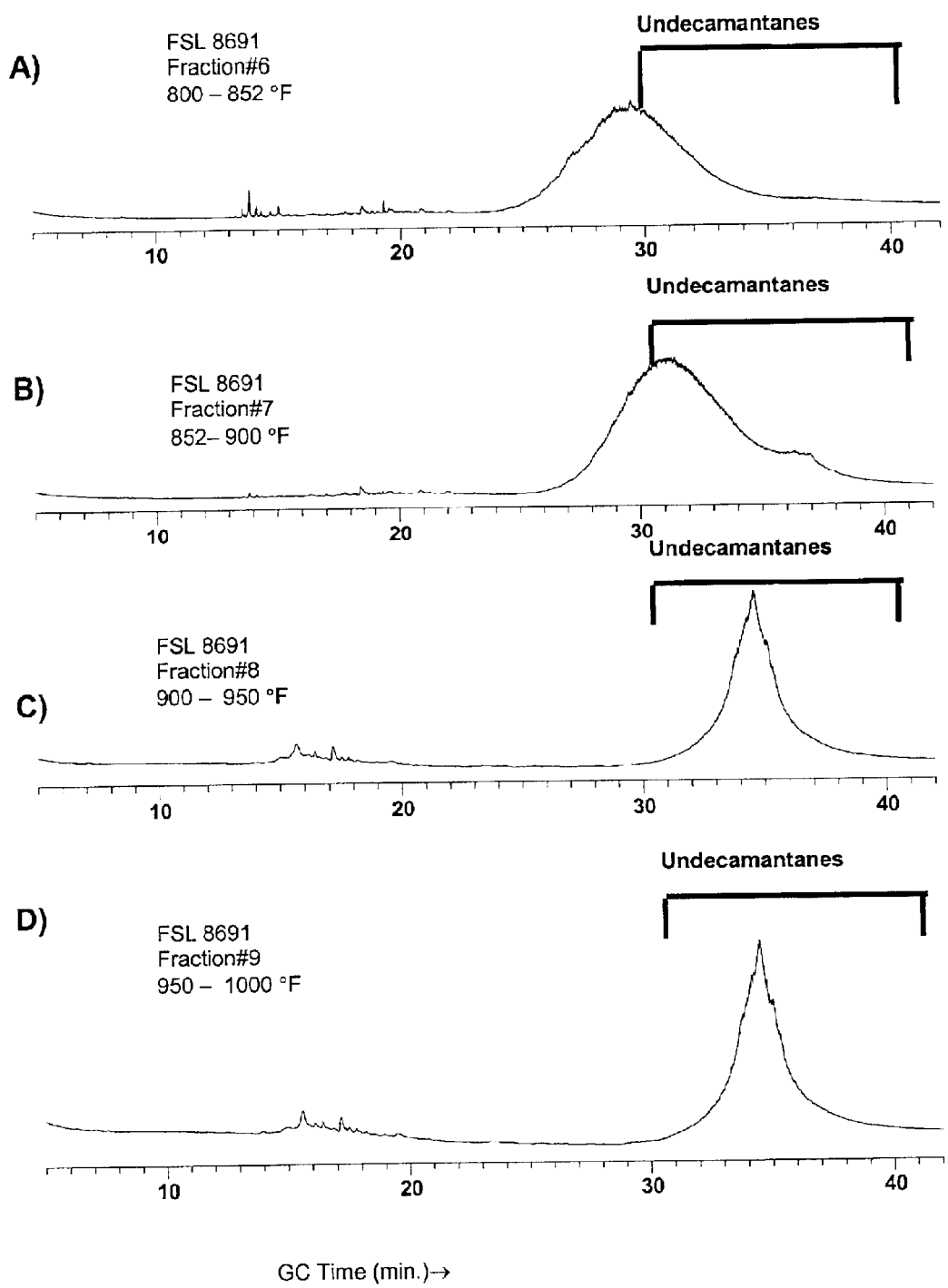
FIGS. 8 (A, B, C, D) illustrates the gas chromatograms of vacuum distillate Fractions #6, #7, #8 and #9 of Feedstock B atmospheric distillation 650° F.+bottoms illustrated in FIG. 7 and exemplified in Example 1.

Additionally, Feedstock B was distilled into fractions containing higher diamondoids guided by a high temperature simulated distillation curve (FIG. 7). Comparison of FIGS. 6 and 8 shows that Feedstock B contains impurities not present in Feedstock A. The feed to the high temperature distillation process was the atmospheric 650° F.+bottoms. Whole Feedstock B distillation reports are given in Tables 2A&B. Tables 3A&B, illustrate the distillation reports for Feedstock B 643° F.+distillation bottoms.

TABLE 2A

Distillation Report for Feedstock B (FSL #8471)
Feedstock B
Column Used: Clean 9" × 1.4" Protruded Packed

| | VAPOR TEMP | | DISTILLATION RECORD | | | | NORMALIZED | | ACTUAL | |
|---|---|---|---|---|---|---|---|---|---|---|
| CUT | ST – END | | WEIGHT G | VOLUME ml @ 60° F. | API 60/60 | DENSITY @ 60° F. | WT PCT | VOL PCT | WT PCT | VOL PCT |
| 1 | 226 – | 349 | 67.0 | 80 | 38.0 | 0.8348 | 7.61 | 8.54 | 7.39 | 8.26 |
| 2 | 349 – | 491 | 507.7 | 554 | 22.8 | 0.9170 | 57.65 | 59.12 | 55.98 | 57.23 |
| 3 | 491 – | 643 | 269.6 | 268 | 9.1 | 1.0064 | 30.62 | 28.60 | 29.73 | 27.69 |
| COL HOLDUP | | | 0.2 | 0 | 6.6 | 1.0246 | 0.02 | 0.00 | 0.02 | 0.00 |
| BTMS | 643 + | | 36.1 | 35 | 6.6 | 1.0246 | 4.09 | 3.74 | 3.98 | 3.62 |
| EOR TRAPS | | | 0.0 | 0 | | | 0.00 | 0.00 | | 0.00 |
| TOTALS | | | 880.6 | 937 | | | 100.00 | 100.00 | 97.09 | 96.80 |
| LOSS | | | 26.4 | 31 | | | | | 2.91 | 3.20 |
| FEED | | | 907.0 | 968 | 19.5 | 0.9371 | | | 100.00 | 100.00 |
| BACK CALCULATED API AND DENSITY | | | | | 19.1 | 0.9396 | | | | |

TABLE 2B

Distillation Report for Feedstock B (FSL #8471)
Feedstock B
Column Used: Clean 9" × 1.4" Protruded Packed

| TEMPERATURE DEGREES F. | | | | | | | API GRAVITIES | | | |
|---|---|---|---|---|---|---|---|---|---|---|
| VAPOR | | | | | | | | OBSERVED | | |
| VLT | ATM EQV. | POT | PRESSURE TORR | REFLUX RATIO | CUT NO | VOLUME ml @ 60° F. | WEIGHT G | HYD RDG | TEMP ° F. | 60° F. |
| 93 | 225.8 | 262 | 50.000 | 3:1 | | | START OVERHEAD | | | |
| 198 | 349.1 | 277 | 50.000 | 3:1 | 1 | 80 | 67.0 | 39.6 | 80.0 | 38.0 |
| 321 | 490.8 | 376 | 50.000 | 3:1 | 2 | 554 | 507.7 | 24.1 | 80.0 | 22.8 |
| | | | Cut 2 looks Milky, White crystals form in Run Down Line. Heat Lamp applied to drip tube. | | | | | | | |
| | | | Cool to transfer btms to smaller flask. | | | | | | | |
| 208 | 437.7 | 323 | 10.000 | 3:1 | | | START OVERHEAD | | | |
| 378 | 643.3 | 550 | 10.000 | 3:1 | 3 | 268 | 269.6 | 9.9 | 75.0 | 9.1 |
| | | | | | | Shutdown due to dry pot | | | | |
| | | | END OF RUN TRAPS | | | 0 | 0.0 | | | |
| | | | VOLUME DISTILLED | | | 902 | | | | |
| | | | COLUMN HOLDUP | | | 0 | 0.2 | 0.0 | 0.0 | 6.6 |
| | | | BOTTOMS | | | 35 | 36.1 | 7.2 | 72.0 | 6.6 |
| | | | RECOVERED | | | 937 | 880.6 | | | |
| | | | FEED CHARGED | | | 968 | 907.0 | 20.7 | 80.0 | 19.5 |
| | | | LOSS | | | 31 | 26.4 | | | |

TABLE 3A

Vacuum Distillation Report for Feedstock B (FSL #8691)
Feedstock B - Atmospheric distillation resid 650° F. + bottoms
Column Used: Sarnia Hi Vac

| TEMPERATURE DEGREES F. | | | | | | | API GRAVITIES | | |
|---|---|---|---|---|---|---|---|---|---|
| VAPOR | | | | | VOL | | OBSERVED | | |
| VLT | ATM EQV. | POT | PRESSURE TORR | REFLUX RATIO | CUT NO | ml 60° F. | WEIGHT G | HYD RDG | TEMP ° F. | 60° F. |

| VLT | ATM EQV. | POT | PRESSURE TORR | REFLUX RATIO | CUT NO | ml 60° F. | WEIGHT G | HYD RDG | TEMP ° F. | 60° F. |
|---|---|---|---|---|---|---|---|---|---|---|
| 315 | 601.4 | 350 | 5.000 | | | | START OVERHEAD | | | |
| 344 | 636.8 | 382 | 5.000 | | | 300 | READING | | | |
| 342 | 644.9 | 389 | 4.000 | | | 500 | READING | | | |
| 344 | 656.3 | 395 | 3.300 | | 1 | 639 | 666.4 | 7.8 | 138.0 | 4.1 |
| 353 | 680.1 | 411 | 2.500 | | | 400 | READING | | | |
| 364 | 701.6 | 430 | 2.100 | | 2 | 646 | 666.9 | 9.4 | 138.0 | 5.6 |
| 333 | 736.0 | 419 | 0.400 | | | 200 | READING | | | |
| 336 | 751.9 | 432 | 0.300 | | 3 | 330 | 334.3 | 12.4 | 139.0 | 8.3 |
| 391 | 799.9 | 468 | 0.500 | | 4 | 173 | 167.7 | 19.0 | 139.0 | 14.5 |
| 411 | 851.6 | 500 | 0.270 | | 5 | 181 | 167.3 | 26.8 | 139.0 | 21.7 |
| 460 | 899.8 | 538 | 0.360 | | 6 | 181 | 167.1 | 27.0 | 139.0 | 21.9 |
| 484 | 950.3 | 569 | 0.222 | | 7 | 257 | 238.4 | 26.2 | 139.0 | 21.2 |
| Shut down distillation to check pot temperature limits with customer. (Drained trap material 5.3 grams) | | | | | | | | | | |
| 472 | 935.7 | 576 | 0.222 | | | | START OVERHEAD | | | |
| 521 | 976.3 | 595 | 0.340 | | 8 | 91 | 85.4 | 23.7 | 139.0 | 18.9 |
| 527 | 999.9 | 610 | 0.235 | | 9 | 85 | 80.8 | 23.0 | 139.0 | 18.2 |
| 527 | 1025.6 | 624 | 0.130 | | 10 | 98 | 93.8 | 21.6 | 139.0 | 16.9 |

Drained remaining trap material of 16.5 grams (~4 grams of water)

| | | | | | | |
|---|---|---|---|---|---|---|
| MID AND END OF RUN TRAPS | | 20 | 17.8 | (mathematically combined) | | |
| VOLUME DISTILLED | | 2701 | | | | |
| COLUMN HOLDUP | | 4 | 4.0 | 0.0 | 0.0 | 3.4 |
| BOTTOMS | | 593 | 621.8 | 11.0 | 214.0 | 3.4 |
| RECOVERED | | 3298 | 3311.7 | | | |
| FEED CHARGED | | 3298 | 3326.3 | 18.0 | 234.0 | 8.6 |
| LOSS | | −5 | 14.6 | | | |

TABLE 3B

Distillation Report for Feedstock B-btms (FSL #8691)
Feedstock B - Atmospheric distillation resid 650° F. + bottoms
Column Used: Sarnia HiVac

| CUT | VAPOR TEMP ST – END | | | WEIGHT G | VOLUME ml @ 60° F. | API 60/60 | DENSITY 60° F. | WT PCT | VOL PCT | WT PCT | VOL PCT |
|---|---|---|---|---|---|---|---|---|---|---|---|
| 1 | 601 | – | 656 | 666.4 | 639 | 4.1 | 1.0435 | 20.12 | 19.38 | 20.03 | 19.40 |
| 2 | 656 | – | 702 | 666.9 | 646 | 5.6 | 1.0321 | 20.14 | 19.59 | 20.05 | 19.62 |
| 3 | 702 | – | 752 | 334.3 | 330 | 8.3 | 1.0122 | 10.09 | 10.01 | 10.05 | 10.02 |
| 4 | 752 | – | 800 | 167.7 | 173 | 14.5 | 0.9692 | 5.06 | 5.25 | 5.04 | 5.25 |
| 5 | 800 | – | 852 | 167.3 | 181 | 21.7 | 0.9236 | 5.05 | 5.49 | 5.03 | 5.50 |
| 6 | 852 | – | 900 | 167.1 | 181 | 21.9 | 0.9224 | 5.05 | 5.49 | 5.02 | 5.50 |
| 7 | 900 | – | 950 | 238.4 | 257 | 21.2 | 0.9267 | 7.25 | 7.79 | 7.17 | 7.80 |
| 8 | 950 | – | 976 | 85.4 | 91 | 18.9 | 0.9408 | 2.58 | 2.76 | 2.57 | 2.76 |
| 9 | 976 | – | 1000 | 80.8 | 85 | 18.2 | 0.9452 | 2.44 | 2.58 | 2.43 | 2.58 |
| 10 | 1000 | – | 1026 | 93.8 | 98 | 16.9 | 0.9535 | 2.83 | 2.97 | 2.82 | 2.98 |
| COL HOLDUP | | | | 4.0 | 4 | 3.4 | 1.0489 | 0.12 | 0.12 | 0.12 | 0.12 |
| BTMS | 1026 | + | | 621.8 | 593 | 3.4 | 1.0489 | 18.78 | 17.98 | 18.69 | 18.01 |
| EOR TRAPS | | | | 17.8 | 20 | | | 0.54 | 0.61 | 0.54 | 0.61 |
| TOTALS | | | | 3311.7 | 3298 | | | 100.0 | 100.0 | 99.56 | 100.15 |
| LOSS | | | | 14.6 | −5 | | | | | 0.44 | −0.15 |

TABLE 3B-continued

Distillation Report for Feedstock B-btms (FSL #8691)
Feedstock B - Atmospheric distillation resid 650° F. + bottoms
Column Used: Sarnia HiVac

| CUT | VAPOR TEMP ST – END | WEIGHT G | VOLUME ml @ 60° F. | API 60/60 | DENSITY 60° F. | WT PCT | VOL PCT | WT PCT | VOL PCT |
|---|---|---|---|---|---|---|---|---|---|
| FEED | | 3326.3 | 3293 | 8.6 | 1.0100 | | | 100.00 | 100.00 |
| BACK CALCULATED API & DENSITY | | | | 9.4 | 1.0039 | | | | |

TABLE 4

Partial Elemental Composition of Feedstock B
Analyses on Feedstock B Atmospheric Distillation 650+ F Resid

| Measured | Value |
|---|---|
| Nitrogen | 0.991 wt % |
| Sulfur | 0.863 wt % |
| Nickel | 8.61 ppm |
| Vanadium | <0.2 ppm |

Table 4 illustrates a partial elemental composition of Feedstock B atmospheric distillation (650+F) residue including some of the identified impurities. Table 4 displays the weight percent nitrogen, sulfur, nickel and vanadium present within this feedstock. These materials were removed in subsequent steps.

Step 3:
Removal of Nondiamondoids Using Pyrolysis

This step, uses a reactor to pyrolyze and degrade a portion of the nondiamondoid components while enriching the diamondoids in the residue. Pyrolysis exploits the great thermal stability of undecamantanes relative to non-diamondiod components of the feed material. FIGS. 8 (A,B,C, D) respectively, shows the GC profiles of the distillate fractions #6–9, the undecamantane portions from Feedstock B—Atmospheric distillation 650° F.+bottoms (see FIG. 7 and Table 3A&B).

Figure 10:
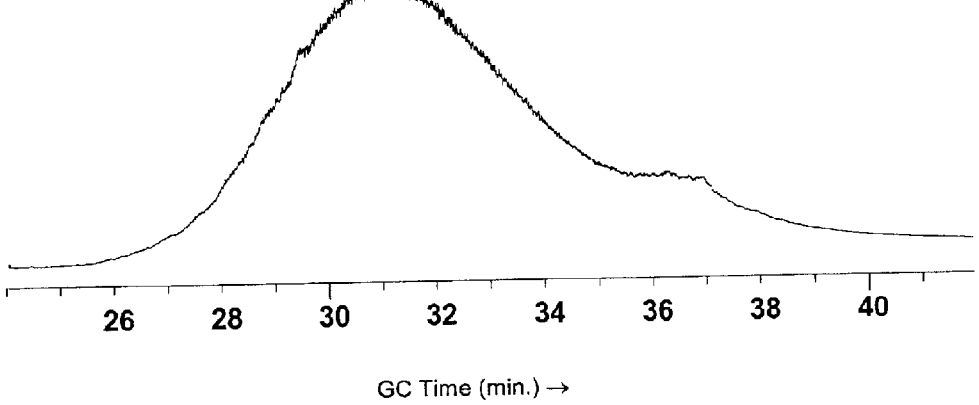
FIGS. 10 (A, B) illustrates the gas chromatograms of the concentration of decamantanes using pyrolysis.

FIG. 10B shows the gas chromatogram of the distillation fraction #7 used as a feed to the pyrolysis unit and FIG. 10A shows the chromatograph of the products of the pyrolytic process. A comparison of the traces in FIGS. 10(A,B) show that the pyrolysis process has removed major nondiamondoid components leaving a residue enriched in undecamantane components. Such reactors can operate at a variety of temperatures and pressures. Pyrolysis can be used to degrade the nondiamondoid components to easily removable gas and coke-like solids facilitating the isolation of undecamantanes.

A PARR® reactor, from PARR INSTRUMENT COMPANY, Moline, Ill., was used to process the distillation fractions obtained from vacuum distillation of a feedstream. For this example, Feedstock B 650° F.+distillation fraction 7 was used as a feedstock for pyrolysis. For enrichment and/or isolation of undecamantanes, the products of four such pyrolysis runs using from 25 to 39 grams each, of Feedstock B 650° F.+distillation fraction 7 were combined. These pyrolysis runs were carried out at temperatures ranging from 410 to 450° C. (higher overall yields of saturated hydrocarbons were found for the lower temperature runs).

Step 4

The higher-diamondoid components enriched following the separation of Step 2 or Step 3, were further treated to concentrate undecamantanes in the following way. In the case of Feedstock A, the distillation fraction of interest for the undecamantane (e.g., the residue left after vacuum distillation fraction 38; a GC profile of this fraction is shown in FIG. 6) is passed through a silica-gel gravity chromatography column to remove aromatic compounds, polar compounds and asphaltenes. The use of a silver nitrate impregnated silica gel provides cleaner diamondoid-containing fractions by removing the free aromatic and polar components. While it is not necessary to use this chromatographic aromatic separation method, it facilitates subsequent steps.

Figure 9:
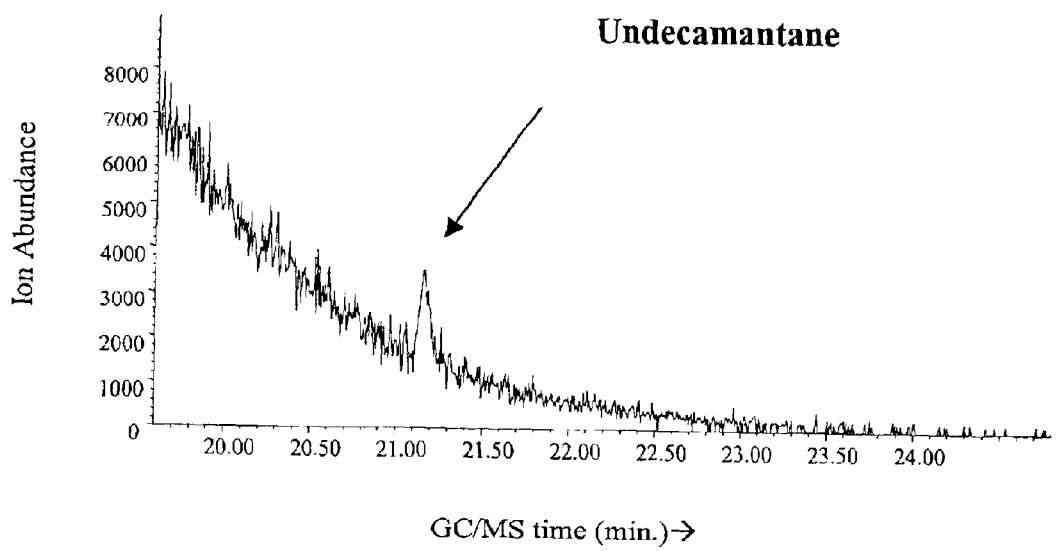
FIGS. 9 (A, B) illustrates the GC/MS selective ion chromatogram (m/z 508) and mass spectrum of pyrolysis product of Feedstock B atmospheric distillation fraction #7 concentratating undecamantanes.
Figure 9:
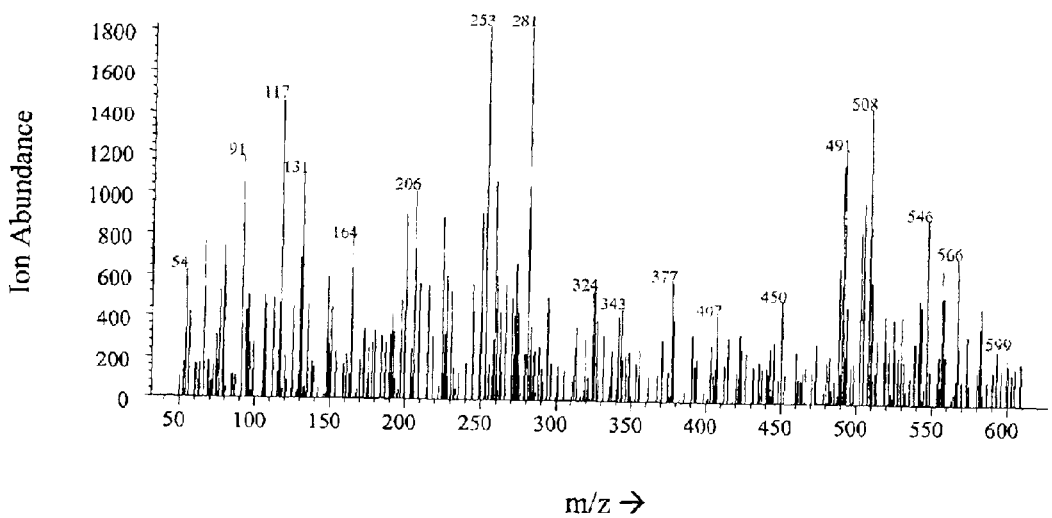

Alternatively, a pyrolysis product (as disclosed above) using distillate fractions of Feedstock B was passed through a silver nitrate impregnated silica-gel gravity chromatography column to remove polar compounds and asphaltenes. The use of a silver nitrate impregnated silica gel provides cleaner diamondoid-containing fractions by removing free aromatic and polar components. In either instance, the distillate fraction or the pyrolysis products can be purified using this step prior to subsequent isolation procedures. The product of this separation was analyzed using GC/MS. A GC/MS analysis using selected ion monitoring of m/z 508 was done to determine elution times for the undecamantane components on our GC/MS system illustrated in FIG. 9. As illustrated in FIG. 9A, the peak eluting at approximately 21 minutes on this GC/MS system correlates to this enriched undecamantane. The mass spectrum in FIG. 9B illustrates the presence of m/z 508 along with a variety of other ions. However, the selected ion chromatograms of ions $117^+$, $206^+$, $253^+$, $281^+$ and $491^+$ suggest these ions are not associated with the peak illustrated in FIG. 9A. This is based on the fact that m/z 117, 206, 253, 281 and 491 ion traces do not show peaks co-eluting with the m/z 508 peak in FIG. 9A.

Example 2

Enrichment of Undecamantanes Using HPLC.

Figure 11:
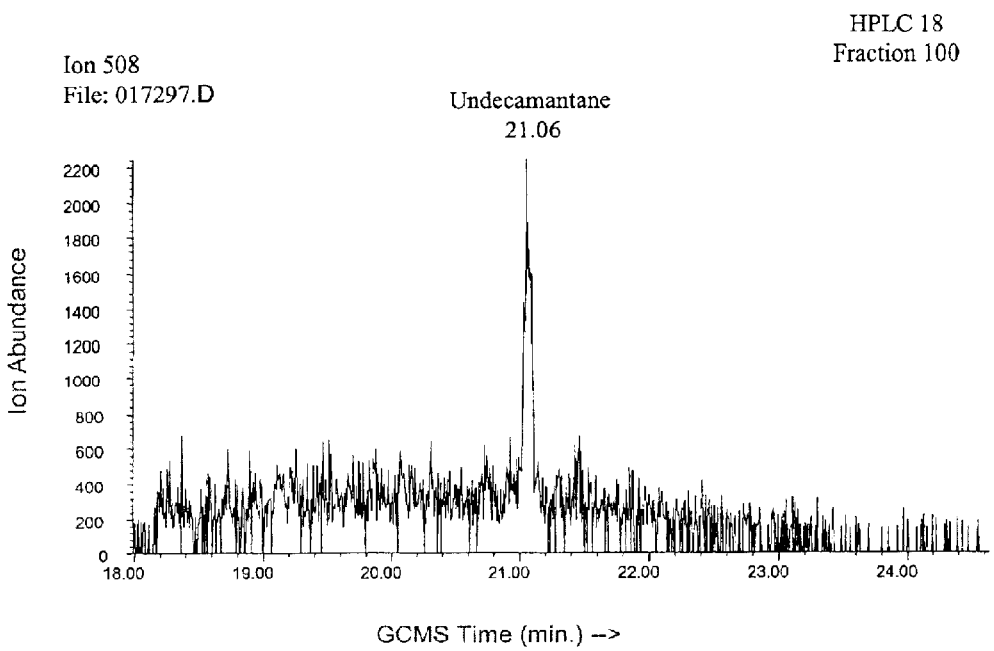
FIG. 11 illustrates results of a preparative HPLC separation of Feedstock B distillate cut #7 pyrolysis product saturated hydrocarbon fraction showing an HPLC fraction taken using octadecyl silane "ODS" columns and acetone mobile phase. This fraction contains undecamantane, molecular weight 508.
Figure 11:
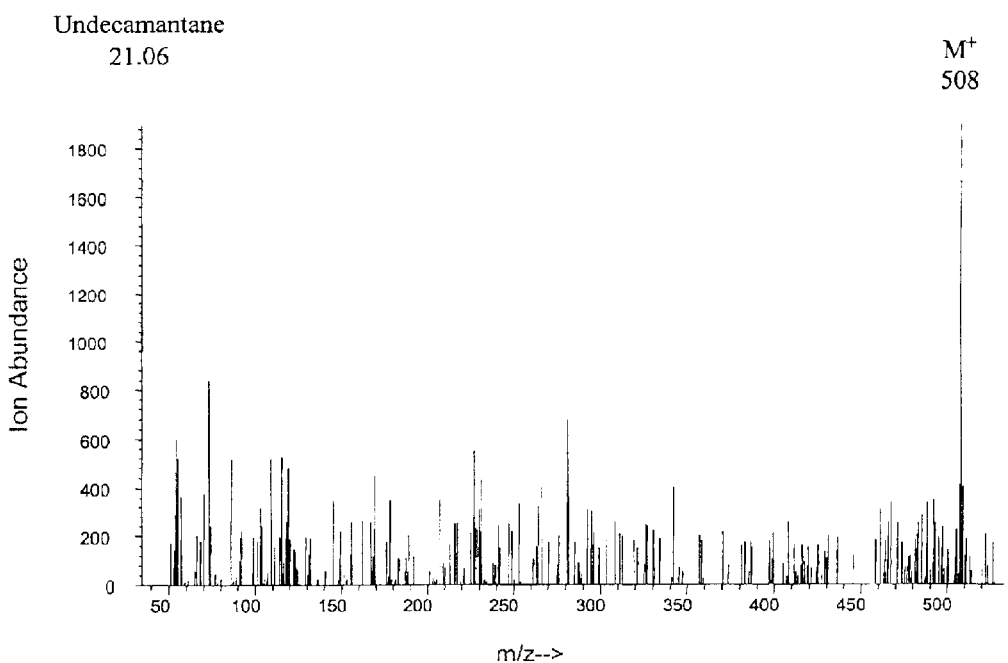

The undecamantane-enriched fraction from Example 1 following steps 1–4 was then subjected to reverse-phase HPLC. Suitable HPLC columns for use are well known to those skilled in the art. In some cases, reverse-phase HPLC with acetone as mobile phase can be used to effect this purification. A preparative ODS HPLC run of Feedstock B distillate cut 7 pyrolysis product saturated hydrocarbon fraction was performed and the HPLC chromatogram recorded using a differential refractometer. HPLC fractions were analyzed by GC/MS to determine undecamantane HPLC elution times (FIG. 11) and monitor purity. The HPLC columns used were two 50 cm×20 mm I.D. WHATMAN octadecyl silane (ODS) columns operated in series (Whatman columns are manufactured by Whatman Inc., USA). A 500 microliter sample of an acetone solution of the cut 7 pyrolysis product saturated hydrocarbon fraction (25 mg) was injected into the columns. The columns were set-up using acetone at 5.00 ml/min as a mobile phase carrier. As seen from a comparison of the chromatograms of FIGS. 9 and 11, the additional isolation step of HPLC significantly enriched the 508 molecular weight undecamantane. More than 100 HPLC fractions were analyzed by GC/MS to determine the GC retention times of individual undecamantanes. Similar assays, as above, could be prepared for the other molecular weight undecamantanes which are anticipated to elute in higher fractions in this HPLC system.

Example 3

Isolation of Undecamantanes Using HPLC and Preparative GC.

Figure 12:
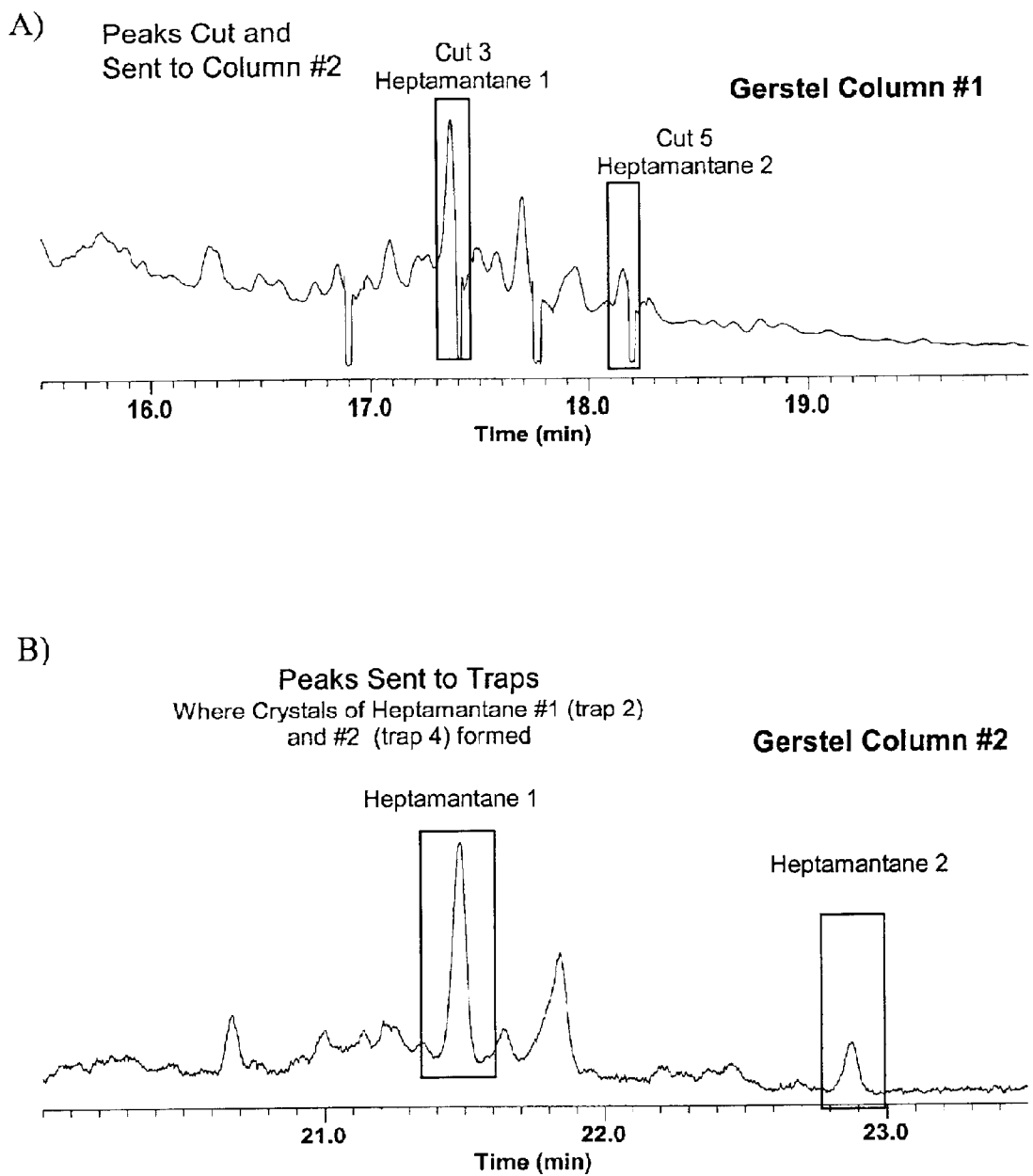
FIGS. 12 (A, B) illustrates the preparative capillary gas chromatographic data for heptamantane isolations.

Using retention times and GC patterns determined from GC/MS analysis as set forth in Example 2, a two-column preparative capillary gas chromatograph is used to isolate undecamantanes from the HPLC fractions. This methodology was demonstrated for heptamantanes as illustrated in FIG. 12. In this example the cut times for the heptamantanes were set for the first preparative capillary GC column, methyl silicone DB-1 equivalent, using the retention times and patterns from a GC/MS assay. The results are shown in the top of FIG. 12A, identified as "peaks cut and sent to column 2" which contains two of the heptamantane from Feedstock B. The preparative capillary gas chromatograph used was manufactured by Gerstel, Inc., Baltimore, Md., USA. However, other gas chromatographs could be used.

Figure 13:
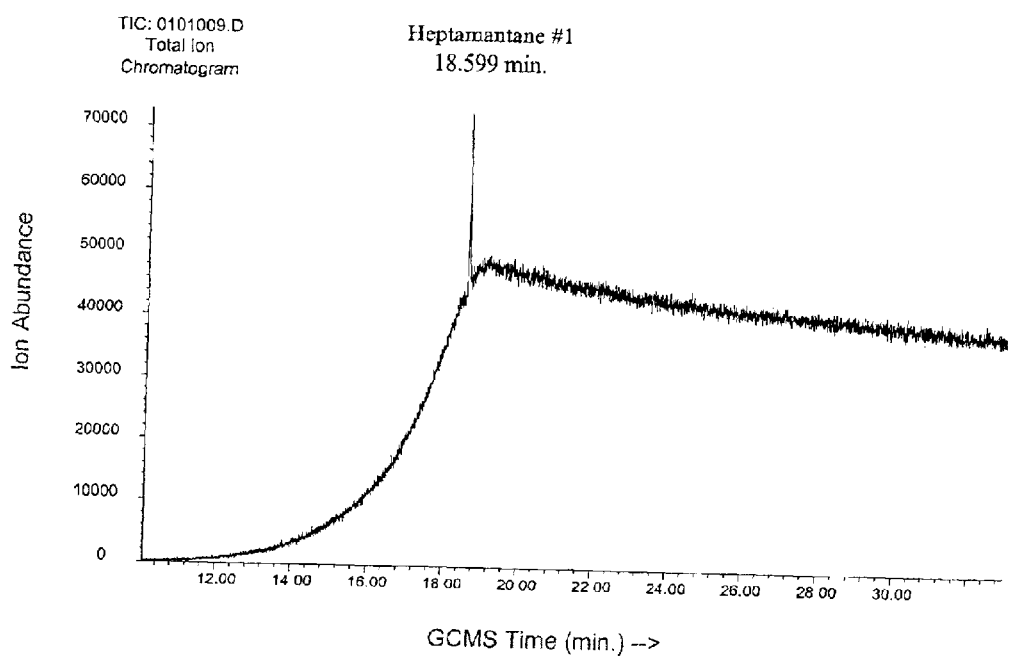
FIGS. 13 (A, B) illustrates the GC/MS total ion chromatogram and mass spectrum of heptamantane #1 isolated by preparative capillary gas chromatography.
Figure 13:
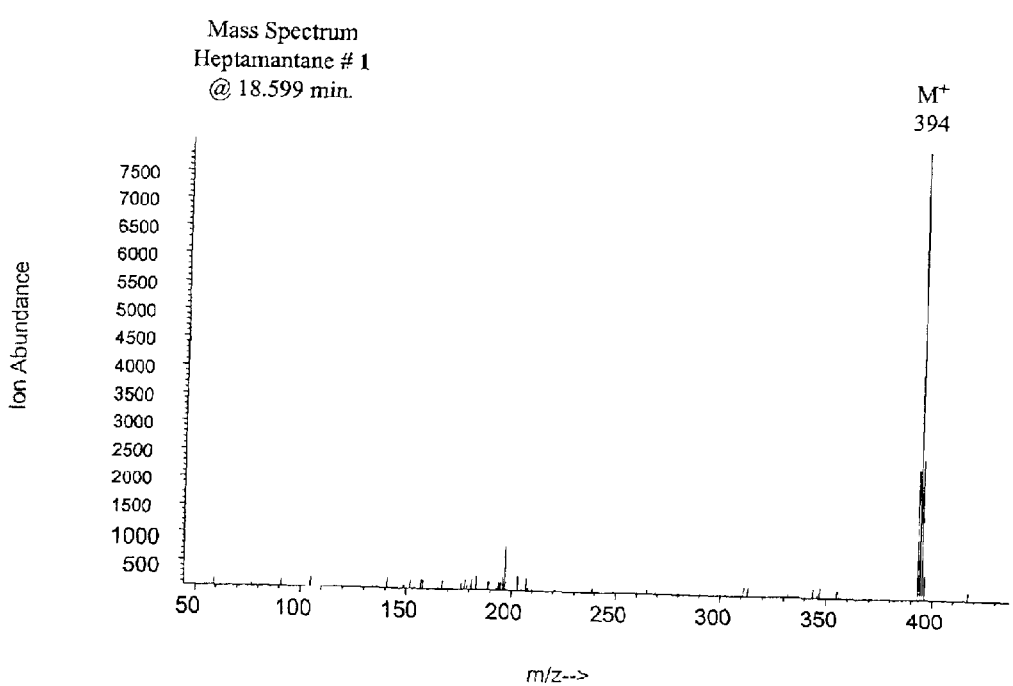
Figure 14:
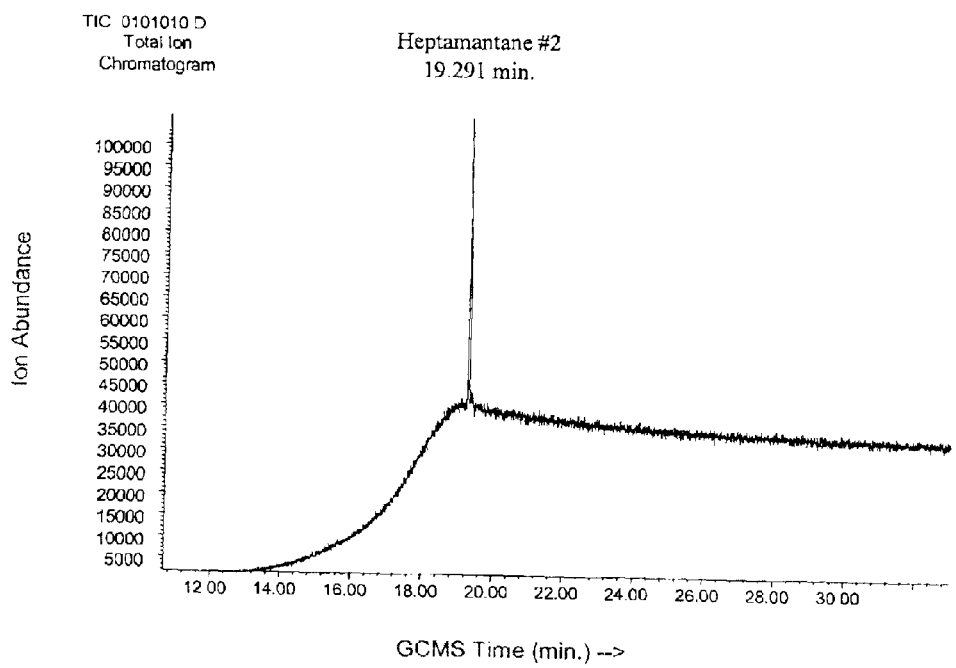
FIGS. 14 (A, B) illustrates the GC/MS total ion chromatogram and mass spectrum of heptamantane #2 isolated by preparative capillary gas chromatography.
Figure 14:
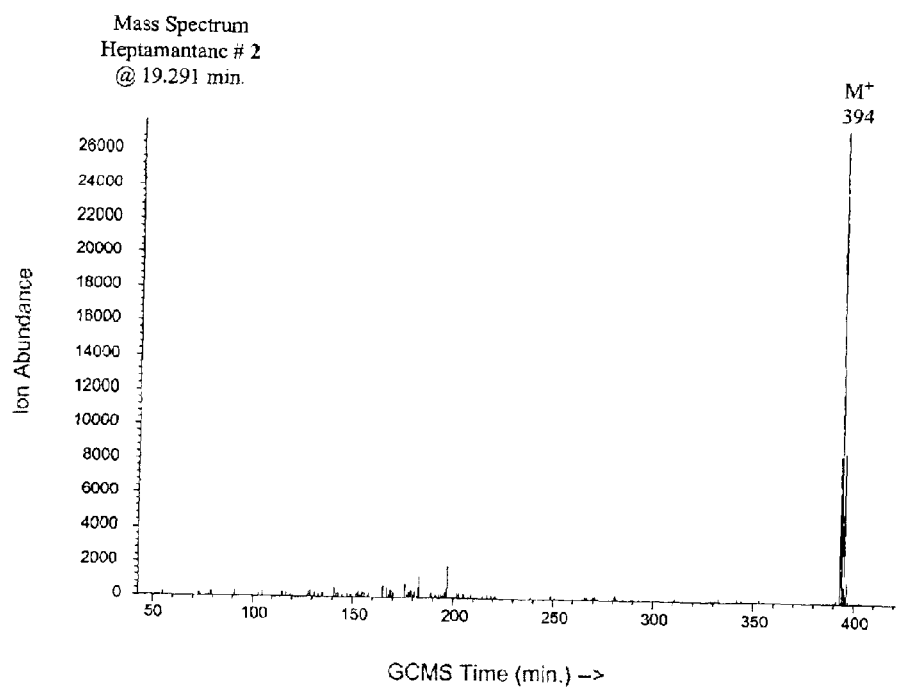

The first column was used to concentrate the heptamantanes by taking cuts that were then sent to the second column (see FIG. 12B illustrated for heptamantane #1 and #2). The second column, phenyl-methyl silicone a DB-17 equivalent, further separated and purified the heptamantanes and then was used to isolate peaks of interest and retain them into individual vials (traps 1–6). GC trap fraction 2 was collected and further processed for the separation of heptamantane #1. GC trap fraction 4 was collected and further processed for the separation of heptamantane #2. Subsequent GC/MS analysis of trap #2 material (FIG. 13) showed it to be heptamantane #1 based upon the earlier run GC/MS assay. Similarly, the GC/MS analysis of trap #4 material (FIG. 14) showed it to be heptamantane #2. This procedure can easily be used to isolate undecamantanes from HPLC fractions such those shown in FIG. 11.

Figure 15:
FIG. 15 illustrates a photomicrograph of heptamantane #1 crystals isolated from Feedstock B by preparative capillary gas chromatography.
Figure 15:
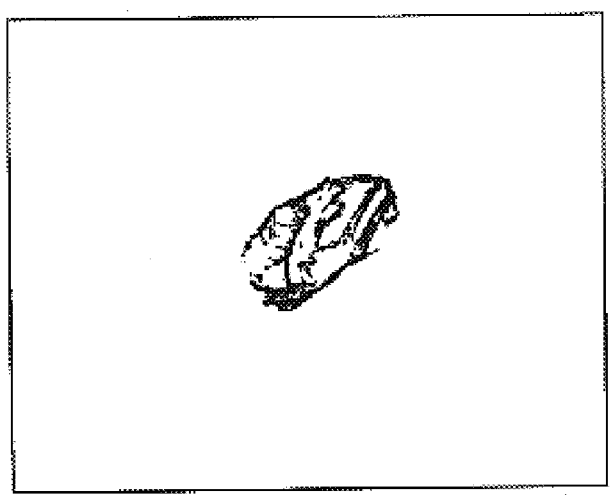
Figure 16:
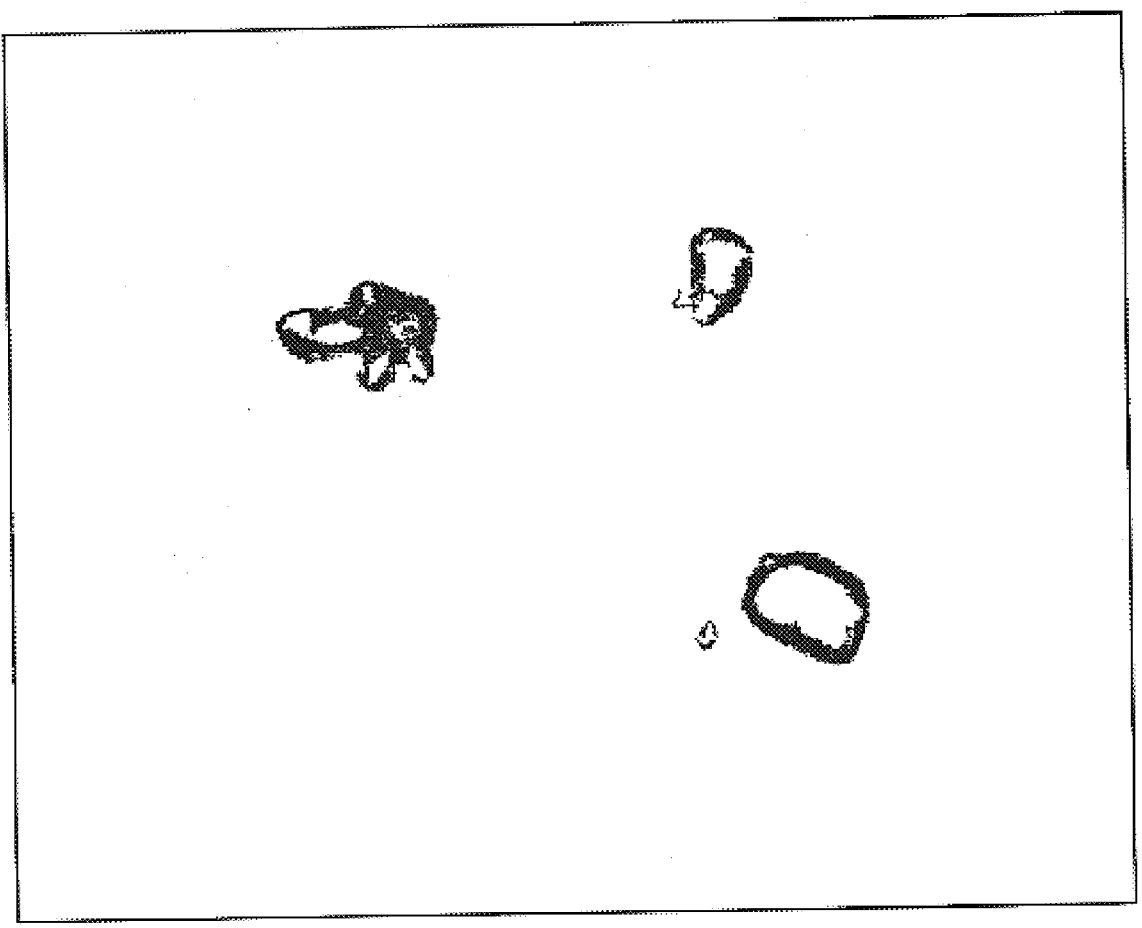
FIG. 16 illustrates a photomicrograph of heptamantane #2 crystals isolated from Feedstock B by preparative capillary gas chromatography.

The highly concentrated heptamantanes were then allowed to crystallize either directly in the trap or from solution. Under the microscope at 30× magnification, the crystals of heptamantane #1 were visible in preparative GC trap fraction 2 (see FIG. 15). These crystals were perfectly clear and showed high refractive index. Crystals of heptamantane #1 had never existed before this isolation. FIG. 16 is a photomicrograph of heptamantane #2 that crystallized in preparative GC trap 4. Crystals of heptamantane #2 had never existed before this isolation. Where concentrations are not high enough for crystallization to occur, further concentration by preparative GC may be necessary.

Example 4

Purification of Single Isomers Using Dual Column Selectivity

As shown in Example 2, some undecamantanes can be enriched by using a single type of HPLC column. For isolation in high purity of undecamantane components, multiple HPLC columns can be employed. This methodology was demonstrated using decamantane with HPLC columns of different selectivities used in succession to isolate a single decamantane. A similar approach is employed for the isolation and/or enrichment of undecamantane. For enrichment of decamantane, the first HPLC system consisted of two Whatman M20 10/50 ODS columns operated in series using acetone as mobile phase at 5.00 mL/min. The detector used was a differential refractometer. From this HPLC run, the decamantane containing fractions 74–83 were combined for further purification on a second HPLC system. Five such runs were completed and all decamantane containing fractions from the runs were combined. This combined fraction contained a molecular weight 456 decamantane and various impurities.

To purify the combined HPLC fractions 74–83 from the ODS, we injected a 50 microliter sample of approximately 1 mg of ODS HPLC combined fraction in acetone/methylene chloride (70:30 volume percent) onto two Hypercarb columns, 4.6 mm I.D.×200 mm, operated in series using acetone/methylene chloride (above) at 1.00 mL/min as mobile phase (@480 psi), and using a differential refractometer detector.

Figure 17:
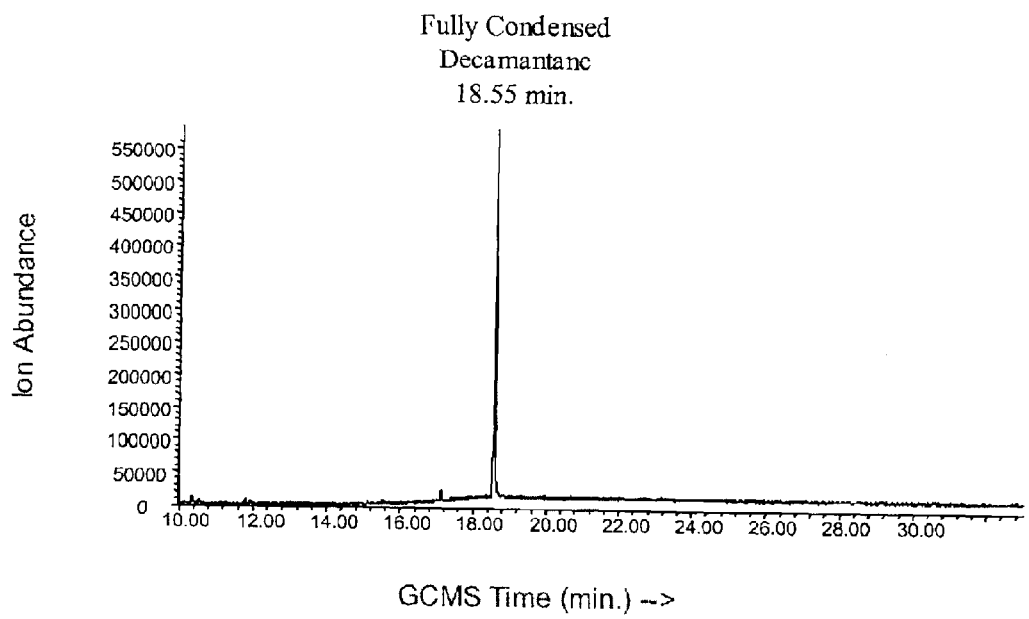
FIGS. 17 (A, B) illustrates GC/MS total ion chromatogram (TIC) and mass spectrum of [1231241(2)3], molecular weight 456, decamantane isolated using two different HPLC columns.
Figure 17:
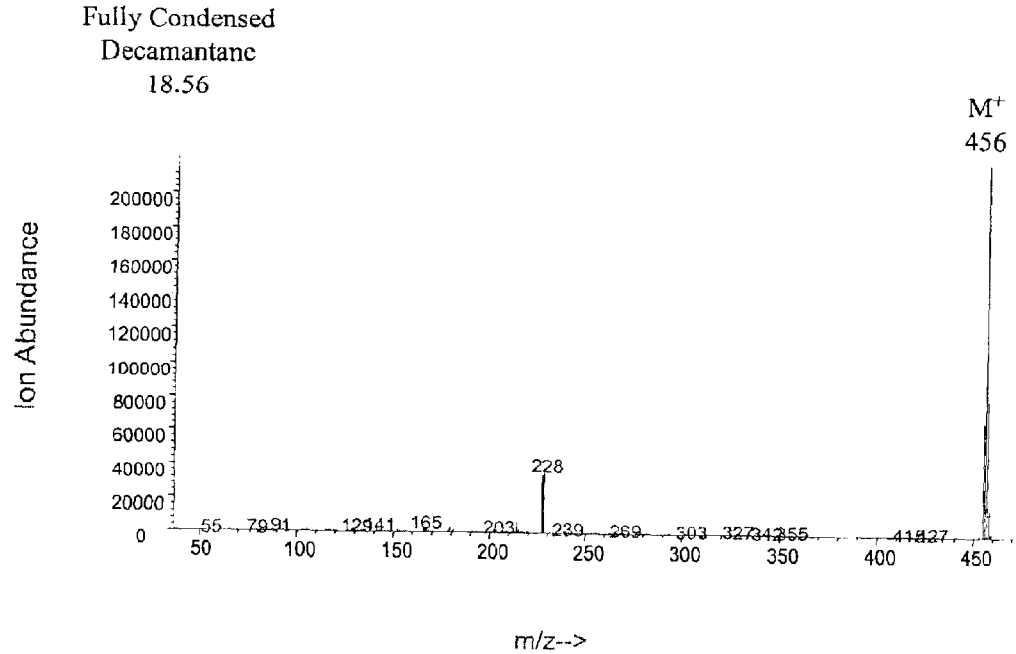
Figure 18:
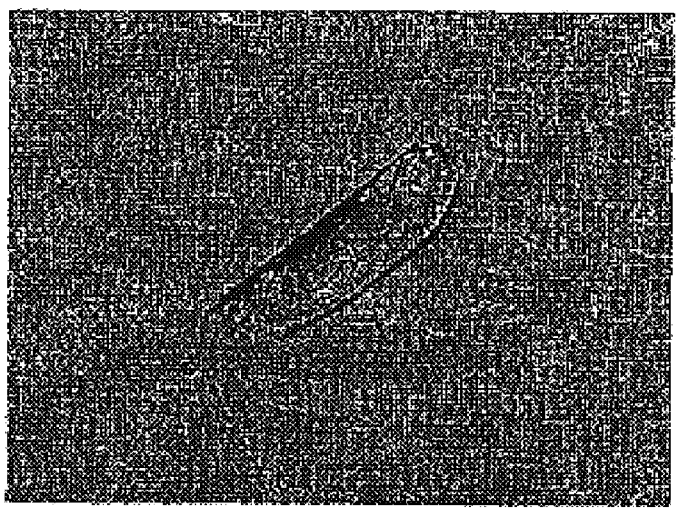
FIGS. 18 (A,B) illustrates a photomicrograph of [1231241 (2)3], molecular weight 456, decamantane crystal and a mass spectra of the dissolved crystal.
Figure 18:
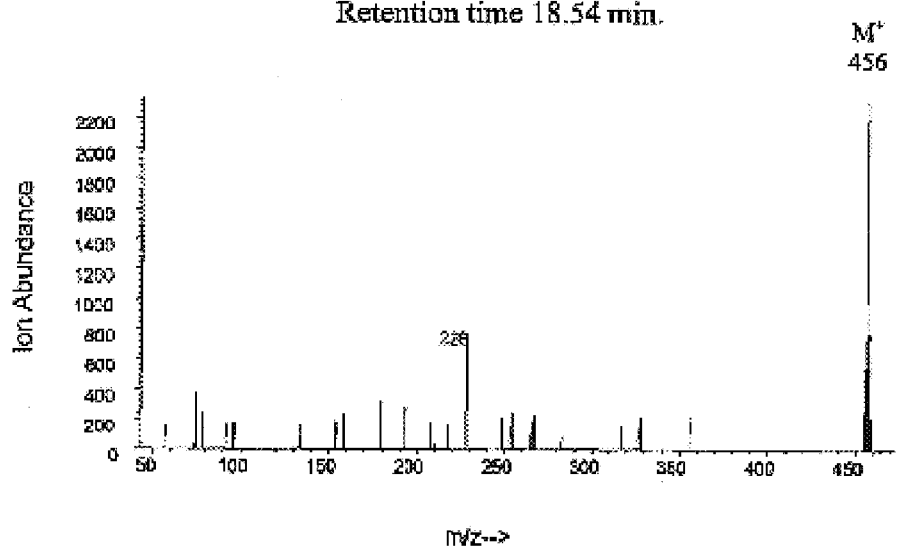

FIG. 17 shows the GC/MS total ion chromatogram (TIC) of the concentrated decamantane containing Hypercarb HPLC fraction eluting at 18.55 minutes. The lower half of FIG. 17 illustrates the mass spectrum of the GC/MS peak with a prominent peak at m/z 456. The resulting decamantane crystal and mass spectrum is shown in FIG. 18.

Undecamantanes could be isolated with a similar methodology as above, i.e. fractionating undecamantane containing ODS HPLC fractions (as shown in Example 2) using columns with different selectivities, such as the Hypercarb or other suitable columns. This method could be repeated to isolate the undecamantanes with molecular weights of 656 and/or 602, as well as molecular weights 642,628, 588, 548 or 534 which respectively are anticipated to be in lower abundance in our feedstocks. FIGS. 20–30 illustrate various structural models exemplifying these molecular weight undecamanantanes. Note that enantiomeric decamantanes are not resolved in GS/MS however, these enantiomers can be isolated by chiral separation methods.

Example 5

Isolation of Substituted Undecamantanes

This example is to illustrate the separation of substituted undecamantanes from Feedstock containing substituted undecamantanes, for example Feedstock A and B. These naturally occurring substituted undecamantanes have uses similar to the unsubstituted undecamantanes and can be de-alkylated to yield the corresponding unsubstituted undecamanante. Accordingly, methods for the isolation of individual substituted undecamantanes were devised and are exemplified herein.

Figure 19:
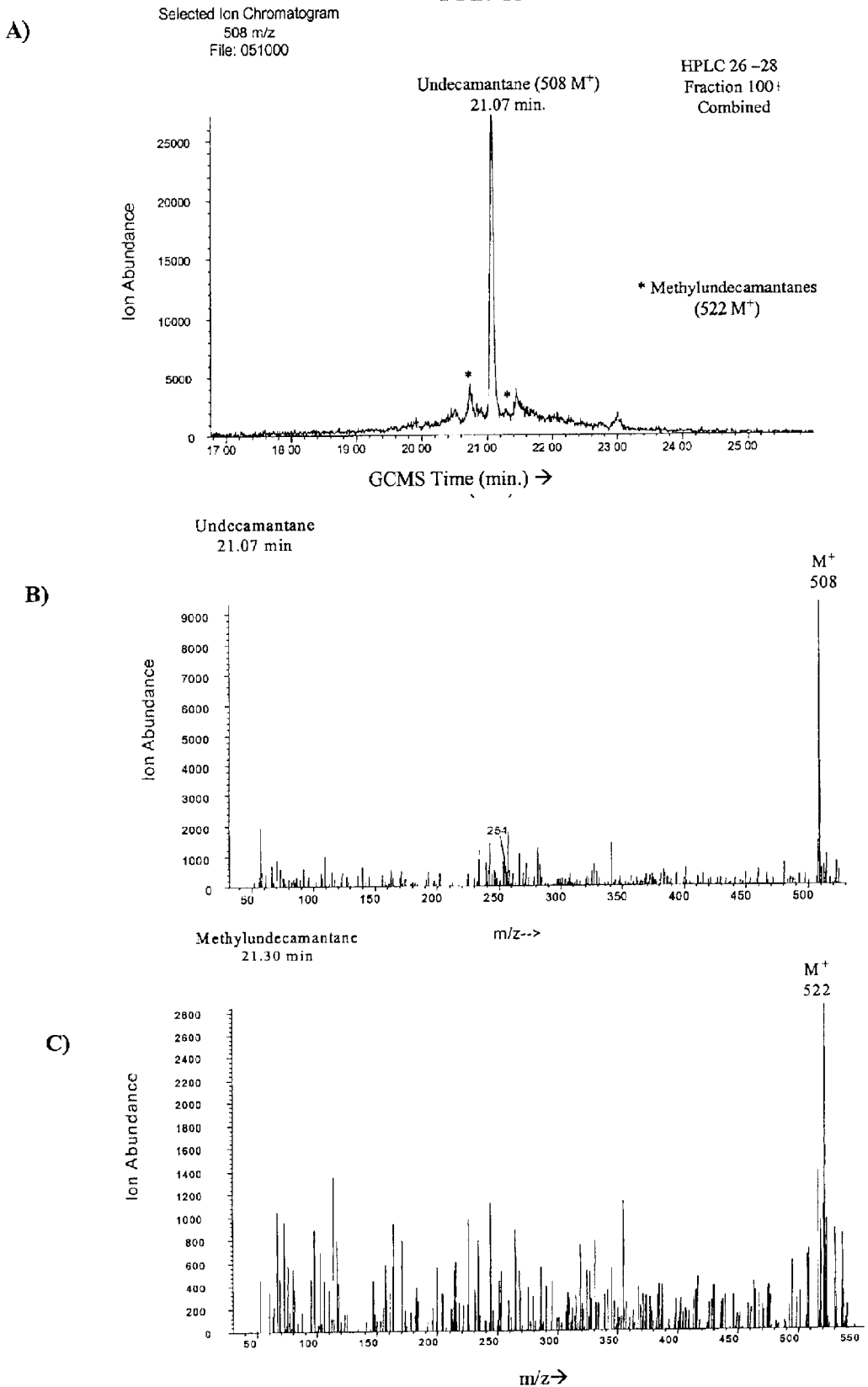
FIGS. 19 (A, B,C) illustrates GC/MS selected ion chromatogram (m/z 508) and mass spectrum of an undecamantane component (mol. wt. 508) and the mass spectrum of a methylundecamantane component (mol. wt. 522).

Alkylundecamantanes can be purified using similar methodologies to those described in Examples 3 and 4. FIGS. 19(A/B/C) shows that the combined ODS 100+ fractions of pyrolysis product of distillate fraction #7 contains methylated undecamantanes. One type of monomethylated undecamantane has a molecular weight of 522 (yielding a mass spectrometric molecular ion of m/z 522) illustrated in FIG. 19. Also, where more than one alkylundecamantane is present in an ODS or Hypercarb HPLC fraction, an additional HPLC separation of that fraction or an alternative preparative GC procedure (as in Example 3) can yield high-purity alkylundecamantanes.

FIGS. 19(A,B,C) shows the presence of undecamanatane, eluting on this GC/MS system at 21.07 minutes and alkylundecamantanes eluting at about 20.7 and 21.30 minutes as illustrated by the asterisks on this chromatogram. FIG. 19(A) is an m/z 508 selected ion chromatogram of the undecamantane eluting at 21.07 minutes. FIG. 19(B) is the spectra of undecamantane, the major component (peak) at 21.07 minutes. FIG. 19(C) shows the spectra of the methylundecamantane which appears as a small peak on the m/z 508 ion chromatogram at 21.30 minutes as a result of it having a m/z 508 fragment ion. This even number fragment is the result of the tendency of diamondoids to have large m+1 ions. In the present case, this refers to the m/z 507 undecamantane fragment plus one.

What is claimed is:

1. A composition comprising diamondoids wherein at least about 25 weight percent of the diamondoids are one or more undecamantane components.
2. A composition of claim 1 wherein from 50 to 100 weight percent of the diamondoids are one or more undecamantane components.
3. A composition of claim 1 wherein from 70 to 100 weight percent of the diamondoids are one or more undecamantane components.
4. A composition of claim 1 wherein from 95 to 100 weight percent of the diamondoids are one or more undecamantane components.
5. A composition of claim 1 wherein from 99 to 100 weight percent of the diamondoids are one or more undecamantane components.
6. The composition of any of claims 1–5, wherein the one or more undecamantane components are a single undecamantane component.
7. The composition of any of claims 1–5 wherein the one or more undecamantane components are isolated optical isomers.
8. The composition of any of claims 1–5, wherein the one or more undecamantane components are isomeric undecamantane components.
9. The composition of any of claims 1–5, wherein the one or more undecamantane component are one or more isomeric undecamantane components represented by the formula $C_{39}H_{40}$.
10. The composition of any of claims 1–5, wherein the one or more undecamantane components are one or more isomeric undecamantane components represented by the formula $C_{41}H_{42}$.
11. The composition of any of claims 1–5, wherein the one or more undecamantane components are one or more nonisomeric undecamantane components represented by the formula $C_{42}H_{44}$.
12. The composition of any of claims 1–5, wherein the one or more undecamantane components are one or more nonisomeric undecamantane components represented by the formula $C_{45}H_{48}$.
13. The composition of any of claims 1–5, wherein the one or more undecamantane components are one or more nonisomeric undecamantane components represented by the formula $C_{48}H_{52}$.
14. The composition of any of claims 1–5, wherein the one or more undecamantane components are one or more nonisomeric undecamantane components represented by the formula $C_{48}H_{52}$.
15. The composition of any of claims 1–5, wherein the one or more undecamantane components are one or more nonisomeric undecamantane components represented by the formula $C_{49}H_{54}$.
16. The composition of any of claims 1–5, wherein the one or more undecamantane components are one or more nonisomeric undecamantane components represented by the formula $C_{50}H_{56}$.
17. The composition of any of claims 1–5 wherein the undecamantane components comprise unsubstituted undecamantane components.
18. The composition of any of claims 1–5 wherein the undecamantane components comprise substituted undecamantane components having from 1 to 10 alkyl substituents.
19. A composition comprising at least about 10% by weight of one or more undecamantane components.
20. The composition of claim 19 containing from 50 to 100% by weight of one or more undecamantane components.
21. The composition of claim 19 containing from 70 to 100% by weight of one or more undecamantane components.
22. The composition of claim 19 containing from 95 to 100% by weight of one or more undecamantane components.
23. The composition of claim 19 containing from 99 to 100% by weight of one or more undecamantane components.
24. The composition of claims 19–23 wherein the one or more undecamantane components are a single undecamantane component.
25. An enriched undecamantane component.
26. The enriched undecamantane component of claim 25 exhibiting a purity of at least 25%.
27. The enriched undecamantane component of claim 25 wherein the undecamantane component is an unsubstituted undecamantane component.
28. The enriched undecamantane component of claim 25 wherein the undecamantane component is a substituted undecamantane component.
29. The enriched undecamantane components of claim 28 wherein the substituted undecamantane component contains from 1 to 10 alkyl substituents.
30. The enriched undecamantane component of claim 29 wherein the substituted undecamantane component is a monomethylated undecamantane component.
31. The enriched undecamantane component of claim 25 in crystalline form.
32. A process for recovering a composition enriched in one or more undecamantane components which process comprises:
    a. selecting a feedstock comprising recoverable amounts of undecamantane components and nonundecamantane components;
    b. removing from the feedstock a sufficient amount of nonundecamantane components having boiling points less than the lowest boiling point undecamantane component under conditions to form a treated feedstock enriched in undecamantane components which can be recovered;
    c. recovering a composition enriched in one or more undecamantane components from said treated feedstock formed in b) above with one or more additional separation techniques selected from the group consisting of chromatographic techniques, thermal diffusion techniques, zone refining, progressive recrystallization and size separation techniques.
33. A process for recovering a composition enriched in undecamantane components which process comprises:
    a. selecting a feedstock comprising recoverable amounts of undecamantane components and nonundecamantane components including nondiamondoid components;

b. removing from the feedstock a sufficient amount of nonundecamantane components having a boiling point-less than the lowest boiling point undecamantane component under conditions to form a treated feedstock enriched in undecamantane components which can be recovered;

c. thermally degrading said treated feedstock to pyrolyze at least a sufficient amount of nondiamondoid components therefrom under conditions to form a thermally treated feedstock retaining recoverable amounts of undecamantane;

d. recovering a composition enriched in one or more undecamantane components from said thermally treated feedstock formed in c) above with one or more additional separation techniques selected from the group consisting of chromatographic techniques, thermal diffusion techniques, zone refining, progressive recrystallization and size separation techniques.

34. A process for recovering a composition enriched in one or more undecamantane components which process comprises:

a. selecting a feedstock comprising recoverable amounts of undecamantane components and nonundecamantane components including nondiamondoid components;

b. thermally degrading said feedstock to pyrolyze at least a sufficient amount of nondiamondoid components therefrom under conditions to provide a thermally created feedstock retaining recoverable amounts of undecamantane;

c. removing from the thermally treated feedstock a sufficient amount of nonundecamantane components having a boiling point less than the lowest boiling point of undecamantane component under conditions to form a treated feedstock enriched in undecamantanes components which can be recovered;

d. recovering a composition enriched in one or more undecamantane components from said treated feedstock recovered in c) above with one or more additional separation techniques selected from the group consisting of chromatographic techniques, thermal diffusion techniques, zone refining, progressive recrystallization and size separation techniques.

35. A process for recovering a composition enriched in one or more undecamantane components which process comprises:

a. selecting a feedstock comprising recoverable amounts of undecamantane components and nonundecamantane components;

b. fractionating the feedstock to form one or more cuts enriched in materials having boiling points in the range of from just below the boiling point of the lowest boiling undecamantane component to just above the boiling point of the highest boiling undecamantane component;

c. recovering a composition enriched in one or more undecamantane components from said one or more cuts formed in b) above with one or more additional separation techniques selected from the group consisting of chromatographic techniques, thermal diffusion techniques, zone refining, progressive recrystallization and size separation techniques.

36. A process for recovering a composition enriched in one or more undecamantane components which process comprises:

a. selecting a feedstock comprising recoverable amounts of undecamantane components and nonundecamantane components including nondiamondoid components;

b. fractionating the feedstock to form one or more cuts enriched in materials having boiling points in the range of from just below the boiling point of the lowest boiling undecamantane component to just above the boiling point of the highest boiling undecamantane component;

c. thermally degrading one or more cuts said to pyrolyze at least a sufficient amount of nondiamondoid components therefrom under conditions to form one or more thermally treated cuts retaining recoverable amounts of undecamantane;

d. recovering a composition comprising one or more undecamantane components from one or more said thermally treated cuts formed in c) above with one or more additional separation techniques selected from the group consisting of chromatographic techniques, thermal diffusion techniques, zone refining, progressive recrystallization and size separation techniques.

37. A process for recovering a composition enriched in one or more undecamantane components which process comprises:

a. selecting a feedstock comprising recoverable amounts of undecamantane components and nonundecamantane compounds including nondiamondoid components;

b. thermally degrading said feedstock to pyrolyze at least a sufficient amount of nondiamondoid components therefrom under conditions to provide a thermally treated feedstock retaining recoverable amounts of undecamantane;

c. fractionating the thermally treated feedstock to form one or more cuts enriched in materials having boiling points in the range of from just below the boiling point of the lowest boiling undecamantane component to just above the boiling point of the highest boiling undecamantane component;

d. recovering a composition enriched in one or more undecamantane components from one or more cuts formed c) above with one or more additional separation techniques selected from the group consisting of chromatographic techniques, thermal diffusion techniques, zone refining, progressive recrystallization and size separation techniques.

38. The process according to any of claims 35–37 wherein said boiling point range is a range having atmospheric equivalents of between about 300 to about 675° C.

39. The process according to any of claims 32–37 wherein said separation technique is a chromatographic technique.

40. The process according to claim 39 wherein said chromatographic technique is selected from the group consisting of liquid chromatography, preparative gas chromatography and high performance liquid chromatography.

41. The process according to claim 39 wherein said additional separation technique is high performance liquid chromatography comprising one or more high performance liquid chromatography columns.

42. The process according to claim 41 wherein the high performance liquid chromatography columns are selected to have a different specificity to the undecamantane components.

\* \* \* \* \*